US007329401B2

(12) United States Patent
Toyokuni et al.

(10) Patent No.: US 7,329,401 B2
(45) Date of Patent: Feb. 12, 2008

(54) CYCLOOXYGENASE-2 SELECTIVE AGENTS USEFUL AS IMAGING PROBES AND RELATED METHODS

(75) Inventors: Tatsushi Toyokuni, Sherman Oaks, CA (US); Nagichettiar Satyamurthy, Los Angeles, CA (US); Harvey R. Herschman, Los Angeles, CA (US); Michael E. Phelps, Encino, CA (US); Jorge R. Barrio, Agoura Hills, CA (US)

(73) Assignee: The Regents of the University of California, Oakland, CA (US)

( * ) Notice: Subject to any disclaimer, the term of this patent is extended or adjusted under 35 U.S.C. 154(b) by 48 days.

(21) Appl. No.: 10/341,316

(22) Filed: Jan. 10, 2003

(65) Prior Publication Data

US 2007/0286801 A1   Dec. 13, 2007

Related U.S. Application Data

(60) Provisional application No. 60/372,858, filed on Apr. 15, 2002.

(51) Int. Cl.
*A61K 51/00*   (2006.01)
*A61M 36/14*   (2006.01)
(52) U.S. Cl. .................. 424/1.81; 424/1.11; 424/1.65; 424/1.85; 424/1.89
(58) Field of Classification Search ............... 424/1.89, 424/1.85, 1.81, 1.11, 1.65, 1.37, 9.1; 514/406
See application file for complete search history.

(56) References Cited

U.S. PATENT DOCUMENTS

| | | | |
|---|---|---|---|
| 3,644,499 A | 2/1972 | Murphy et al. | |
| 3,647,858 A | 3/1972 | Hinkley et al. | |
| 3,707,475 A | 12/1972 | Lombardino | |
| 3,743,656 A | 7/1973 | Brown et al. | |
| 3,901,908 A | 8/1975 | Fitzi et al. | |
| 3,984,431 A | 10/1976 | Gueremy et al. | |
| 4,011,328 A | 3/1977 | Pinhas et al. | |
| 4,051,250 A | 9/1977 | Dahm et al. | |
| 4,146,721 A | 3/1979 | Rainer | |
| 4,302,461 A | 11/1981 | Cherkofsky | |
| 4,372,964 A | 2/1983 | Whitney | |
| 4,381,311 A | 4/1983 | Haber | |
| 4,427,693 A | 1/1984 | Haber | |
| 4,472,422 A | 9/1984 | Whitney | |
| 4,503,065 A | 3/1985 | Wilkerson | |
| 4,533,666 A | 8/1985 | Matsumoto et al. | |
| 4,576,958 A | 3/1986 | Wexler | |
| 4,590,205 A | 5/1986 | Haber | |
| 4,632,930 A | 12/1986 | Carini et al. | |
| 4,686,231 A | 8/1987 | Bender et al. | |
| 4,820,827 A | 4/1989 | Haber | |
| 4,822,805 A | 4/1989 | Takasugi et al. | |
| 4,914,121 A | 4/1990 | Sawai et al. | |
| 5,051,518 A | 9/1991 | Murray et al. | |
| 5,134,142 A | 7/1992 | Matsuo et al. | |
| 5,169,857 A | 12/1992 | Angerbauer et al. | |
| 5,344,991 A | 9/1994 | Reitz et al. | |
| 5,380,738 A | 1/1995 | Norman et al. | |
| 5,401,765 A | 3/1995 | Lee | |
| 5,434,178 A | 7/1995 | Talley et al. | |
| 5,739,166 A | 4/1998 | Reitz et al. | |
| 5,859,257 A | 1/1999 | Talley | |
| 6,045,773 A | 4/2000 | Isakson et al. | |
| 6,469,040 B2 * | 10/2002 | Seibert et al. | 514/406 |

FOREIGN PATENT DOCUMENTS

| | | |
|---|---|---|
| DE | 199 28 742 A1 | 12/1999 |
| EP | 0 372 445 B1 | 6/1990 |
| EP | 0 592 664 B1 | 4/1994 |
| WO | WO 92/05162 A1 | 4/1992 |
| WO | WO 92/19604 A1 | 11/1992 |
| WO | WO 93/14082 A1 | 7/1993 |
| WO | WO 94/15932 A1 | 7/1994 |
| WO | WO 94/27980 A1 | 12/1994 |
| WO | WO 95/00501 A2 | 1/1995 |
| WO | WO 95/00501 A3 | 1/1995 |
| WO | WO 96/03387 A1 | 2/1996 |

(Continued)

OTHER PUBLICATIONS

Sugawara, et al.; *Rapid detection of human infections with fluorine-18 fluorodeoxyglucose and positron emission tomography: preliminary results*; European Journal of Nuclear Medicine; vol. 25, No. 9, Sep. 1998, 1238-1243; © Springer-Verlag 1998.
Stumpe, et al.; *Infection imaging using whole-body FDG-PET*; European Journal of Nuclear Medicine; vol. 27, No. 7, Jul. 2000, pp. 822-832; Jul. 2000; © Springer-Verlag 1998.
McCarthy, et al.; *Radiosynthesis, Biodistribution and Pet Imaging of Potent and Selective Inhibitors of Cyclooxygenase-1 and Cyclooxygenase-2*; Proceedings of the 42nd Annual Meeting, Scientific Papers, No. 194; vol. 36, No. 5, p. 49P, May 1995.
McCarthy, et al.; *Radiosynthesis, In Vitro Validation, and In Vivo Evaluation of $^{18}$F-Labeled COX-1 and COX-2 Inhibitors*; The Journal of Nuclear Medicine; vol. 43, No. 1, pp. 117-124; Jan. 2002.
De Vries, et al.; *Labeling of Cyclooxygenase-2 Inhibitors DuP-697 and ITS Desbromo Derivative: The Crucial Role of the Solvent.*; J. Labelled Cpd. Radiopharm., Symposium Abstracts; vol. 44, Suppl. 1, pp. S933-S935; 2001.

(Continued)

*Primary Examiner*—Dameron L. Jones
(74) *Attorney, Agent, or Firm*—Christie, Parker & Hale, LLP.

(57) ABSTRACT

This invention provides novel cyclooxygenase-2 selective agents that are particularly useful as imaging probes in non-invasive imaging techniques, such as PET and SPECT. Preferred cyclooxygenase-2 selective agents inhibit cyclooxygenase-2 activity with greater potency and specificity than conventional cyclooxygenase-2 inhibitors. Other aspects of the invention include pharmaceutical compositions including the cyclooxygenase-2 selective agents as well as methods for detecting and/or inhibiting cyclooxygenase-2. These methods are particularly useful for diagnosing and treating disorders, such as inflammation, which is characterized by elevated cyclooxygenase-2 levels.

39 Claims, No Drawings

FOREIGN PATENT DOCUMENTS

| WO | WO 96/03388 A1 | 2/1996 |
| --- | --- | --- |
| WO | WO 96/03392 A1 | 2/1996 |
| WO | WO 96/24584 A1 | 8/1996 |
| WO | WO 96/24585 A1 | 8/1996 |
| WO | WO 96/25405 A1 | 8/1996 |
| WO | WO 97/14679 A2 | 4/1997 |
| WO | WO 97/14679 A3 | 4/1997 |
| WO | WO 00/18730 A1 | 4/2000 |

OTHER PUBLICATIONS

Penning, et al.; *Synthesis and Biological Evaluation of the 1,5-Diarylpyrazole Class of Cyclooxygenase-2 Inhibitors: Identification of 4-[5-(4-Methylphyenyl)-3-(trifluoromethyl)-1H-Methylphenylpyrazol-1-yl]benzenesulfonamide (SC-58635, Celecoxib)*; J. Med. Chem; vol. 40, pp. 1347-1365; © 1997 American Chemical Society.

Gans, et al.; *Anti-Inflammatory and Safety Profile of DuP 697, a Novel Orally Effective Prostaglandin Synthesis Inhibitor*; The Journal of Pharmacology and Experimental Therapeutics; vol. 254, No. 1, pp. 180-187; © 1990 The American Society for Pharmacology and Experimental Therapeutics.

Talley, et al,; *4-[5-Methyl-3-phenylisoxazol-4-yl]-benzenesulfonamide, Valdecoxib: A Potent and Selective Inhibitor of COX-2*; J. Med. Chem.; vol. 43, pp. 775-777; © 2000 American Chemical Society.

Ding, et al.; *Mechanistic Positron Emission Tomography Studies of 6-[$^{18}$F]Fluorodopamine in Living Baboon Heart: Selective Imaging and Control of Radiotracer Metabolism Using the Deuterium Isotope Effect*; Journal of Neurochemistry; vol. 65, No. 2, pp. 682-690; © 1995 International Society for Neurochemistry.

Staley, et al; *Comparison of [$^{18}$F]altanserin and [$^{18}$F]deuteroaltanserin for PET imaging of serotonin $_{2A}$ receptors in baboon brain: pharmacological studies*; Nuclear Medicine and Biology; vol. 28, pp. 271-279; © 2001 Elsevier Science Inc.

Haka, et al.; *Aryltrimethylammonium Trifluoromethanesulfonates as Precursors to Aryl [$^{18}$F]Fluorides: Improved Synthesis of [$^{18}$F]GBR-13119*; Journal of Labelled Compounds and Radiopharmaceuticals; vol. XXVII, No. 7, pp. 823-833; © 1989 John Wiley & Sons, Ltd.

Fingl, et al.; *The Pharmacological Basis of Therapeutics, Section 1, Introduction and Chapter 1 General Principles*; Pharmacokinetics; pp. 1-46; 1975.

Maclaren, et al.; *Repetitive, non-invasive imaging of the dopamine $D_2$ receptor as a reporter gene in living animals*; Gene Therapy; vol. 6, pp. 785-791; © 1999 Stockton Press.

Kumar, et al.; *Convenient Approach to 3,4-Diarylisoxazoles Based on the Suzuki Cross-Coupling Reaction*; Adv. Synth. Catal.; vol. 344, No. 10, pp. 1146-1151; © 2002 Wiley-VCH Verlag GmbH & Co. KGaA.

Damhaut, et al.; *No-Carrier-Added Asymmetric Synthesis of α-Methyl-α-Amino Acids Labelled with Fluorine-18*; Tetrahedron; vol. 53, No. 16, pp. 5785-5796; © 1997 Elsevier Science Ltd.

Miyaura, et al.; *Palladium-Catalyzed Cross-Coupling Reactions of Organoboron Compounds*; Chem. Rev.; vol. 95; pp. 2457-2483; © 1995 American Chemical Society.

Suzuki, A.; *Recent advances in the cross-coupling reactions of organoboron derivaties with organic electrophiles, 1995-1998*; Journal of Organometallic Chemistry; vol. 576; pp. 147-168; © 1999 Elsevier Science S.A.

Reddy, et al.; *Ligand-induced Prostaglandin Synthesis Requires Expression of the TIS10/PGS-2 Prostaglandin Synthase Gene in Murine Fibroblasts and Macrophages*; The Journal of Biological Chemistry; vol. 269, No. 22, Issue of Jun. 3, pp. 15473-15480; © 1994 The American Chemical Society for Biochemistry and Molecular Biology, Inc.

Kilbourn, et al.; *Synthesis of Fluorine-18 Labeled GABA Uptake Inhibitors*; Appl. Radiat. Isot.; vol. 41, No. 9, pp. 823-828; © 1990 Pergamon Press plc.

Habeeb, et al.; *Design and Synthesis of Diarylisoxazoles: Novel Inhibitors of Cyclooxygenase-2 (COX-2) With Analgesic-Antiinflammatory Activity*; Drug Development Research; Vo. 51, pp. 273-286; © 2001 Wiley-Liss, Inc.

Kilbourn, et al.; *Fluorine-18 Labeling of Proteins*; The Journal of Nuclear Medicine; vol. 28, No. 4, pp. 462-470; Apr. 1987.

Song, et al.; *Regiospecific Mono-ispo-Iodination of 3,4-Bis(trimethylsilyl)furan and Regiospecific ipso-Iodination of Tris[(4-alkyl- or -aryl)furan-3-yl]boroxines to 4-Substituted 3-(Trimethylsilyl)furans and Unsymmetrical 3,4-Disubstituted Furans*; Liebigs Ann. Chem.; pp. 29-34; © 1994 Verlagsgellschaft mbH.

Hamacher, et al.; *Efficient Stereospecific Synthesis of No-Carrier-Added 2-[$^{18}$F]-Fluoro-2-Deoxy-D-Glucose Using Aminopolyether Supported Nucleophilic Substitution*; The Journal of Nuclear Medicine; vol. 27, No. 2, pp. 235-238; 1986.

Baldwin, et al.; *Syntheses of Racemic and Both Chiral Forms of Cyclopropane-1,2-$d_2$ and Cyclopropane-1-$^{13}$C-1,2,3-$d_3$*; J. Am. Chem. Soc.; vol. 114, No. 24, pp. 9401-9408; © 1992 American Chemical Society.

Tewson, et al.; *Synthesis and Biodistribution of R- and S-Isomers of [$^{18}$F]-Fluoropropranolol, a Lipophilic Ligand for the β-Adrenergic Receptor*; Nuclear Medicine & Biology; vol. 26, pp. 891-896; © Elsevier Science Inc.

De Vries, et al.; *Synthesis and Evaluation of [$^{18}$f]-Desbromo-DUP-697 as PET Tracer for Cyclooxygenase-2 Expression*;J. Label Compd. Radiopharm 2003: 46:S1-S403; p. S95 (Abstract).

\* cited by examiner

CYCLOOXYGENASE-2 SELECTIVE AGENTS USEFUL AS IMAGING PROBES AND RELATED METHODS

CROSS-REFERENCE TO RELATED APPLICATIONS

This application claims the benefit of U.S. Provisional Application No. 60/372,858, filed Apr. 15, 2002.

FIELD OF THE INVENTION

This invention relates to novel cyclooxygenase-2 selective agents, particularly cyclooxygenase-2 inhibitors, useful as imaging probes for positron emission tomography (PET) and single photon emission computed tomography (SPECT), as well as to related diagnostic and therapeutic methods.

BACKGROUND OF THE INVENTION

During the past two decades several radioactive probes have been developed for scintigraphic imaging of inflammation. Scintigraphic detection is based on local physicochemical changes and is consequently superior to radiological techniques, including X-ray computed tomography, magnetic resonance imaging and ultrasonography, which rely on anatomical changes. Scintigraphic techniques can, for example, be used to detect early inflammation, when anatomical structures have not yet been altered. Two types of radioactive probes are currently used for scintigraphic imaging of inflammation. One type of probe shows increased extravasation at the site of inflammation due to the locally enhanced vascular permeability. The second probe utilizes the diapedesis and chemotaxis of leukocytes, namely radiolabeled white blood cells and radiolabeled monoclonal antibodies or radiolabeled peptide ligands that target, respectively, leukocyte antigens or receptors. All of these probes are radiolabeled with a single photon-emitting isotope and therefore used with single photon emission computed tomography (SPECT). While PET and SPECT detect distribution of radioactive probes, PET has a much greater sensitivity and resolution than SPECT. In addition, PET has the ability to measure the concentration of radioactive probes quantitatively. No PET probes specific for imaging inflammatory processes are currently available. [$^{18}$F]Fluorodeoxyglucose ([$^{18}$F]FDG) has been used to image inflammation using PET [For example, see: (a) Sugawara, Y.; Braun, D. K.; Kison, P. V.; Russo, J. E.; Zasadny, K. R.; Wahl, R. L. "Rapid detection of human infections with fluorine-18 fluorodeoxyglucose and positron emission tomography: preliminary results." *Eur. J. Nucl. Med.* 1998, 25, 1238-1243. (b) Stumpe, K. D.; Dazzi, H.; Schaffner, A.; von Schulthess, G. K. "Infection imaging using whole-body FDG-PET." *Eur. J. Nucl. Med.* 2000, 27, 822-832.]. [$^{18}$F] FDG accumulates at the site of inflammation because of the increased glucose uptake of infiltrated granulocytes and tissue macrophages. However, the glucose uptake occurs in any cell type with high glycolytic activity. In addition, [$^{18}$F]FDG uptake at the site of inflammation is affected by serum glucose levels and by conditions such as diabetes mellitus. These factors limit the use of [$^{18}$F]FDG as a PET imaging probe specific for inflammation.

Since the discovery of cyclooxygenase-2, an inducible form of cyclooxygenase involved in inflammation, a number of reports have appeared on the development of cyclooxygenase-2 selective inhibitors. In 1995, McCarthy et al. reported the $^{18}$F-labeling of a cyclooxygenase-2 selective inhibitor, SC-58125, and its in vivo imaging in a baboon (McCarthy, T. J., et al. (1995) J. Nucl. Med. 36, 49P; see also McCarthy, T. J., et al. (2002) J. Nucl. Med. 43:117-124). However, SC-58125 suffers from a relatively low cyclooxygenase-2 affinity (COX-2 IC$_{50}$=0.10 μM), as well as a long plasma half-life (221 hours in male rat), which are unfavorable properties for PET imaging probes. See T. D. Penning et al. *J. Med. Chem.* 1997, 40, 1347-1365. Consequently, $^{18}$F-labeled SC-58125 has never been further investigated as a PET imaging probe for cyclooxygenase-2 detection. Very recently, de Vries and Vaalburg reported the radiochemical synthesis of $^{18}$F-labeled COX-2 selective inhibitor, DuP-697, and its desbromo derivative by a $^{18}$F for $^{19}$F exchange reaction as potential PET imaging probes for COX-2 [E. F. J. de Vries, W. Vaalburg *J. Labelled Cpd. Radiopharm.* 2001, 44 (Suppl 1), S933-S935]. DuP-697 is however less potent than SC-58125 (prostaglandin synthesis IC$_{50}$>1 μM). See K. R. Gans et al. *J. Pharmacol. Exp. Ther.* 1990, 254, 180-187. Furthermore, the $^{18}$F for $^{19}$F exchange reaction is not suitable for the synthesis of $^{18}$F-labeled compounds with high specific activity (i.e., ~10$^3$-10$^4$ Ci/mmol) required for imaging probes designed to interact with molecular recognition sites, such as COX-2-selective inhibitors that interact with the substrate-binding site of COX-2.

Cyclooxygenase-2 selective agents that are useful as imaging probes would facilitate the in vivo imaging of a variety of inflammatory processes. In addition, novel cyclooxygenase-2 selective agents that selectively inhibit cyclooxygenase-2 activity could be used to treat physiological disorders in which cyclooxygenase-2 is elevated.

SUMMARY OF THE INVENTION

The invention provides cyclooxygenase-2 selective agents. In a first embodiment, the cyclooxygenase-2 selective agent has the formula:

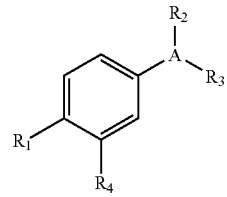

wherein:
A comprises a 4-, 5-, or 6-membered ring selected from a partially unsaturated heterocyclyl, a heteroaryl, a cycloalkenyl, and an aryl;
R$_1$ is selected from methylsulfone and sulfonamide;
R$_2$ comprises a group selected from a heteroaryl, a cycloalkyl, a cycloalkenyl, and an aryl; and
R$_3$ comprises a linear or branched alkyl; and either:
  R$_3$ comprises a radioactive or paramagnetic isotope, and R$_4$ is hydrogen; or
  R$_4$ comprises a radioactive or paramagnetic isotope; and
wherein the cyclooxygenase-2 selective agent is not 4-(5-[$^{18}$F]fluoromethyl-3-phenylisoxazol-4-yl)benzenesulfonamide or 4-(5-[$^{18}$F]fluoroethyl-3-phenylisoxazol-4-yl)benzenesulfonamide.

In one variation of this embodiment, R$_3$ includes a radioactive or paramagnetic isotope, and R$_4$ is hydrogen. For example, R$_3$ can include a radioactive halide. R$_3$ can also (alternatively or additionally include) deuterium, e.g., $R_3$ can be $CD_2{}^{18}F$. It has been reported that 4-(5-methyl-3-phenylisoxazol-4-yl)benzenesulfonamide (valdecoxib) is metabolized in vivo to yield 4-(5-hydroxymethyl-3-phenyl-isoxazol-4-yl)benzenesulfonamide (Talley, J. J.; Brown, D. L.; Carter, J. S.; Graneto, M. J.; Koboldt, C. M.; Masferrer, J. L.; Perkins, W. E.; Rogers, R. S.; Shaffer, A. F.; Zhang, Y. Y.; Zweifel, B. S.; Seivert, K. *J. Med. Chem.* 2000, 43, 775-777). This metabolism involves proton abstraction at the methyl group on the isoxazole ring, presumably via the P450 enzyme-catalyzed oxidation process. The deuterium substitution in the fluoromethyl group slows kinetics of this proton abstraction thus decreasing the rate of metabolism and increasing the bioavailability of the 4-(5-[$^{18}F$, $^2H_2$]fluoromethyl-3-phenylisoxazol-4-yl)benzenesulfonamide [for example, see: (1) Ding, Y. S.; Fowler, J. S.; Gatley, S. J.; Logan, J.; Volkow, N. D.; Shea, C. *J. Neurochem.* 1995, 65, 682-690; (2) Staley, J. K.; Van Dyck, C. H.; Tan, P.-Z.; Tikriti, M. A.; Ramsby, Q.; Klump, H.; Ng, C.; Garg, P.; Soufer, R.; Baldwin, R. M.; Innis, R. B. *Nucl. Med. Biol.* 2001, 28, 271-279].

In another variation of this embodiment, $R_4$ comprises a radioactive or paramagnetic isotope, such as, for example, a radioactive halide. In specific variations of this embodiment, A comprises a 5-membered heterocyclic ring selected from a pyrrolyl, a furyl, an oxazolyl, an isoxazolyl, a thiazolyl, an isothiazolyl, an imidazolyl, and a pyrazolyl, and $R_1$ is sulfonamide or methylsulfone. $R_2$ can be, for example, an unsubstituted aryl.

In specific variations of this embodiment, the cyclooxygenase-2 selective agent includes a radioactive isotope and has a specific activity of at least about $10^3$ Ci/mmol. Exemplary isotopes include $^{11}C$, $^{123}I$, $^{125}I$, $^{73}Se$, $^{76}Br$, $^{77}Br$, and $^{18}F$. In preferred embodiments, the isotope is detectable by PET. In specific embodiments, the cyclooxygenase-2 selective agent is a cyclooxygenase-2 selective inhibitor with an $IC_{50}$ of less than about 10 nM.

Examples of specific radioactively labeled cyclooxygenase-2 selective agents according to this first embodiment of the invention include 2-[$^{18}F$]fluoro-4-(5-methyl-3-phenyl-isoxazol-4-yl)benzenesulfonamide, 3-[4-(methylsulfonyl)phenyl]-4-phenyl-5-[$^{18}F$]trifluoromethylisoxazole, 4-(4-[$^{18}F$]fluorophenyl)-3-[4-(methylsulfonyl)phenyl]-5-trifluoromethylisoxazole, 4-[3-(4-[$^{18}F$]fluorophenyl)-5-methylisoxazol-4-yl]benzenesulfonamide, 4-(5-[$^{18}F$]fluoro-3-phenylisoxazol-4-yl)benzenesulfonamide, and 4-(5-[$^{18}F$, $H_2$]fluoromethyl-3-phenylisoxazol-4-yl)benzenesulfonamide.

The invention also provides a pharmaceutical composition comprising a pharmaceutically acceptable carrier and a diagnostically effective amount of a cyclooxygenase-2 selective agent according to this first embodiment of the invention.

Another aspect of the invention is a method of detecting cyclooxygenase-2. The method entails: (a) adding a cyclooxygenase-2 selective agent according to the first embodiment to a biological sample or administering the cyclooxygenase-2 selective agent to an individual; and (b) detecting the cyclooxygenase-2 selective agent as an indication of cyclooxygenase-2. In a variation of this embodiment, the cyclooxygenase-2 selective agent is administered to an individual, and the radioactive isotope is detectable in vivo. In a preferred variation of this embodiment, in vivo detection is carried out in the individual by PET. In a specific embodiment, the method is employed to detect cyclooxygenase-2 as an indication of inflammation. In exemplary, specific embodiments, cyclooxygenase-2 is detected in an individual is known or suspected to have one or more of the following conditions: inflammation, arthritis, neoplasia, and/or a central nervous system disorder. In preferred embodiments, the cyclooxygenase-2 selective agent is administered to a human.

In a second embodiment, the cyclooxygenase-2 selective agent has the formula:

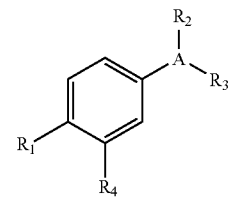

wherein:
A comprises a 4-, 5-, or 6-membered ring selected from a partially unsaturated heterocyclyl, a heteroaryl, a cycloalkenyl, and an aryl;
$R_1$ is selected from methylsulfone and sulfonamide;
$R_2$ comprises an unsubstituted group selected from a heteroaryl, a cycloalkyl, a cycloalkenyl, and an aryl;
$R_3$ comprises a linear or branched alkyl halide; and
$R_4$ is hydrogen; and
wherein the cyclooxygenase-2 selective agent is not 3-[4-(methylsulfonyl)phenyl]-4-phenyl-5-trifluoromethyl-isoxazole, 4-(5-fluoromethyl-3-phenylisoxazol-4-yl)benzenesulfonamide, or 4-(5-fluoroethyl-3-phenylisoxazol-4-yl)benzenesulfonamide.

In specific variations of this embodiment, A comprises a 5-membered heterocyclic ring selected from a pyrrolyl, a furyl, an oxazolyl, an isoxazolyl, a thiazolyl, an isothiazolyl, an imidazolyl, and a pyrazolyl, and $R_1$ can be, for example, sulfonamide. $R_2$ can be, for example, an unsubstituted aryl. In specific variations of this embodiment, the halide is selected from fluorine, chlorine, bromine, and iodine. In specific embodiments, the cyclooxygenase-2 selective agent is a cyclooxygenase-2 selective inhibitor with an $IC_{50}$ of less than about 10 nM.

An exemplary cyclooxygenase-2 selective agent according to this second embodiment of the invention is 2-fluoro-4-(5-methyl-3-phenylsioxazol-4-yl)benzenesulfonamide.

The invention also provides a pharmaceutical composition comprising a pharmaceutically acceptable carrier and a therapeutically effective amount of a cyclooxygenase-2 selective agent according to this second embodiment of the invention.

Another aspect of the invention is a method of inhibiting cyclooxygenase-2, which entails binding cyclooxygenase-2 with a cyclooxygenase-2 selective agent according to the second embodiment. In a variation of this embodiment, cyclooxygenase-2 is bound in vivo, and the method entails administering an effective amount of the cyclooxygenase-2 inhibitor to an individual. In exemplary, specific embodiments, cyclooxygenase-2 is detected in an individual is known or suspected to have one or more of the following conditions: inflammation, arthritis, neoplasia, and/or a central nervous system disorder. In preferred embodiments, the cyclooxygenase-2 selective agent is administered to a human.

DETAILED DESCRIPTION

The novel cyclooxygenase-2 selective agents of the invention can be used to detect cyclooxygenase-2 in vitro or in vivo. Accordingly, the invention includes a cyclooxygenase-2 detection method that has research, as well as diagnostic applications. Cyclooxygenase-2 selective agents with inhibitory activity can be used to inhibit cyclooxygenase-2 in vitro or in vivo. In vivo inhibition of cyclooxygenase-2 activity is beneficial, for example, in the prophylaxis or treatment of physiological disorders characterized by elevated cyclooxygenase-2, typically disorder involving inflammation. For in vivo diagnostic or therapeutic applications, the invention provides pharmaceutical compositions.

I. Definitions

The term "cyclooxygenase-2 selective agent" refers to an agent that selectively binds and/or inhibits the activity of the cyclooxygenase-2 enzyme to a greater degree than the cyclooxygenase-1 enzyme.

A "cyclooxygenase-2 inhibitor" is one that selectively inhibits cyclooxygenase-2 activity, i.e, one that produces greater inhibition of the cyclooxygenase-2 enzyme, compared to the inhibition of the cyclooxygenase-1 enzyme. The difference in inhibition can be about 2-fold, about 5-fold, about 10-fold, about 100-fold, or about 1000-fold or greater. Inhibition of the cyclooxygenase enzyme is generally determined by measuring the $IC_{50}$, i.e., concentration of inhibitor that produces half-maximal inhibition of enzyme activity.

Where used, alone or within other terms such as "haloalkyl," "alkylsulfonyl," "alkoxyalkyl," and "hydroxyalkyl," the term "alkyl" encompasses linear or branched radicals, generally having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, isoamyl, and hexyl.

The terms "sulfonyl" or "sulfone," whether used alone or within other terms such as "alkylsulfone" or "sulfonamide," denote the divalent radical —$SO_2$—.

The term "hydroxyalkyl" encompasses linear or branched alkyl radicals having one to about ten carbon atoms, any one of which can be substituted with one or more hydroxyl radicals. More preferred hydroxyalkyl radicals are "lower hydroxyalkyl" radicals having one to about six carbon atoms and one or more hydroxyl radicals. Examples of such radicals include hydroxymethyl, hydroxyethyl, hydroxypropyl, hydroxybutyl, and hydroxyhexyl.

The term "alkenyl" embraces linear or branched radicals having at least one carbon-carbon double bond of about two to about twenty carbon atoms or, preferably, about two to about twelve carbon atoms. More preferred alkenyl radicals are "lower alkenyl" radicals having about two to about six carbon atoms. The terms "alkenyl" and "lower alkenyl" encompass radicals having "cis" or "trans" orientations, or alternatively, "Z" or "E" orientations. (Z stands for "Zusammen," meaning cis; and E stands for "Entgegen," meaning trans.) Examples of alkenyl radicals include ethenyl, propenyl, allyl, butenyl, and 4-methylbutenyl.

The term "heterocyclyl" encompasses saturated, partially unsaturated and unsaturated heteroatom-containing ring-shaped radicals, where the heteroatoms can, for example, be selected from nitrogen, sulfur, and oxygen. Examples of partially unsaturated heterocyclyl radicals encompass a pyrrolyl, a furyl, an oxazolyl, an isoxazolyl, a thiazolyl, an isothiazolyl, an imidazolyl, and a pyrazolyl. More specific examples include dihydrothiophene, dihydropyran, dihydrofuran, and dihydrothiazole.

Unsaturated heterocyclyl radicals include an unsaturated three- to six-membered heteromonocyclic group containing one to about four nitrogen atoms. The term "unsaturated heterocyclyl radical" also encompasses "heteroaryl" radicals. Examples of unsaturated heterocyclyl radicals within the scope of the invention include, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.; an unsaturated condensed heterocyclyl group containing one to about five nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; an unsaturated three- to six-membered heteromonocyclic group containing an oxygen atom, for example, pyranyl, furyl, etc.; an unsaturated three- to six-membered heteromonocyclic group containing a sulfur atom, for example, thienyl, etc.; an unsaturated three- to six-membered heteromonocyclic group containing one to two oxygen atoms and one to three nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; an unsaturated condensed heterocyclyl group containing one to two oxygen atoms and one to three nitrogen atoms (e.g. benzoxazolyl, benzoxadiazolyl, etc.); unsaturated three- to six-membered heteromonocyclic group containing one to two sulfur atoms and one to three nitrogen atoms, for example, thiazolyl, thiadiazolyl (e.g., 1,2,4-thiadiazolyl, 1,3,4-thiadiazolyl, 1,2,5-thiadiazolyl, etc.) etc.; an unsaturated condensed heterocyclyl group containing one to two sulfur atoms and one to three nitrogen atoms (e.g., benzothiazolyl, benzothiadiazolyl, etc.), and the like. The term also encompasses radicals where heterocyclyl radicals are fused with aryl radicals. Examples of such fused bicyclic radicals include benzofuran, benzothiophene, and the like. The heterocyclyl group can have one to three substituents such as an alkyl, a hydroxyl, a halo, an alkoxy, an oxo, an amino, and an alkylamino group.

The terms "alkoxy" and "alkyloxy" encompass linear or branched oxy-containing radicals each having alkyl portions of one to about ten carbon atoms. More preferred alkoxy radicals are "lower alkoxy" radicals having one to about six carbon atoms. Examples of such radicals include methoxy, ethoxy, propoxy, butoxy, and tert-butoxy groups.

The term "cycloalkyl" includes saturated carbocyclic radicals having about three to about twelve carbon atoms. More preferred cycloalkyl radicals are "lower cycloalkyl" radicals having about three to about eight carbon atoms. Examples of such radicals include cyclopropyl, cyclobutyl, cyclopentyl, and cyclohexyl groups.

The term "cycloalkenyl" encompasses partially unsaturated carbocyclic radicals having about three to twelve carbon atoms. More preferred cycloalkenyl radicals are "lower cycloalkenyl" radicals having about four to about eight carbon atoms. Examples of such radicals include cyclobutenyl, cyclopentenyl, and cyclohexenyl.

The term "aryl," alone or in combination with other terms, means a carbocyclic aromatic system containing one, two, or three rings wherein such rings can be attached together in a pendent manner or can be fused. The term "aryl" encompasses aromatic radicals, such as for example phenyl, naphthyl, tetrahydronaphthyl, indane, and biphenyl. Aryl moieties can also be substituted at a substitutable position with one or more substituents selected independently from an alkyl, an alkoxyalkyl, an alkylaminoalkyl, a carboxyalkyl, an alkoxycarbonylalkyl, an aminocarbonylalkyl, an alkoxy, an aralkoxy, a hydroxyl, an amino, a halo, a nitro, an alkylamino, an acyl, a cyano, a carboxyl, an aminocarbonyl, an alkoxycarbonyl, and an aralkoxycarbonyl.

The term "alkoxyalkyl" encompasses alkyl radicals having one or more alkoxy radicals attached to the alkyl radical, for example, to form monoalkoxyalkyl and dialkoxyalkyl radicals. The "alkoxy" radicals can be further substituted with one or more halo atoms, such as fluoro, chloro or bromo, to provide haloalkoxy radicals. More preferred haloalkoxy radicals are "lower haloalkoxy" radicals having one to six carbon atoms and one or more halo radicals. Examples of such radicals include fluoromethoxy, chloromethoxy, trifluoromethoxy, trifluoroethoxy, fluoroethoxy, and fluoropropoxy groups.

The term "aminoalkyl" encompasses alkyl radicals substituted with amino radicals. More preferred are "lower aminoalkyl" radicals. Examples of such radicals include aminomethyl, aminoethyl, and the like.

The term "alkylamino" denotes amino groups substituted with one or two alkyl radicals. Preferred are "lower N-alkylamino" radicals having alkyl portions having one to about six carbon atoms. Suitable lower alkylamino radicals include mono or dialkylamino groups, such as N-methylamino, N-ethylamino, N,N-dimethylamino, N,N-diethylamino, and the like.

The term "alkylaminoalkyl" encompasses radicals having one or more alkyl radicals attached to an aminoalkyl radical.

The terms "carboxy" or "carboxyl," whether used alone or with other terms, such as "carboxyalkyl," denotes —C(=O)—OH.

The term "carboxyalkyl" encompasses alkyl radicals substituted with a carboxy radical. "Lower carboxyalkyls" include lower alkyl radicals, as defined above, and can be additionally substituted on the alkyl radical with a halide. Examples of such lower carboxyalkyl radicals include carboxymethyl, carboxyethyl, and carboxypropyl.

The term "carbonyl," whether used alone or with other terms, such as "alkoxycarbonyl~, denotes —C(=O)—

The term "aminocarbonyl" denotes an amide group of the formula —C(=O)NHR, e.g., —C(=O)—NH$_2$.

The term "alkoxycarbonyl (ester)" refers to a radical containing an alkoxy radical, as defined above, attached via an oxygen atom to a carbonyl radical. More preferred are "lower alkoxycarbonyl" radicals with alkyl portions having one to about six carbons. Examples of such lower alkoxycarbonyl radicals include substituted or unsubstituted methoxycarbonyl, ethoxycarbonyl, propoxycarbonyl, butoxycarbonyl, and hexyloxycarbonyl.

The term "aralkoxy" refers to an aralkyl radical attached through an oxygen atom to another radical.

The term "aralkyl" encompasses aryl-substituted alkyl radicals, such as benzyl, diphenylmethyl, triphenylmethyl, phenylethyl, and diphenylethyl. The aryl in said aralkyl can be additionally substituted with a halo, an alkyl, an alkoxy, a haloalkyl and/or a haloalkoxy group.

The term "acyl" denotes a radical remaining after removal of a hydroxyl from an organic acid. Examples of such acyl radicals include alkanoyl and aroyl radicals. Examples of "lower alkanoyl" radicals include formyl, acetyl, propionyl, butyryl, isobutyryl, valeryl, isovaleryl, pivaloyl, hexanoyl, and trifluoroacetyl.

The term "aroyl" refers to an aryl radical linked to a carbonyl radical, as defined above. Examples of aroyls include benzoyl, naphthoyl, and the like. The aryl in the aroyl can be additionally substituted.

The term "halide" or "halo" refers to a radical of a halogen, such as fluorine, chlorine, bromine or iodine. The term "haloalkyl" encompasses radicals wherein any one or more of the alkyl carbon atoms is substituted with a halide. Specifically encompassed are monohaloalkyl, dihaloalkyl, and other polyhaloalkyl radicals. A monohaloalkyl radical, for one example, can have either an iodo, bromo, chloro or fluoro atom within the radical. Dihalo and other polyhaloalkyl radicals can have two or more of the same halides or a combination of different halides. "Lower haloalkyls" include those having about one to about six carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, and the like.

A "normal" cell or tissue is one that is free of a particular physiological disorder of interest. Thus, a normal cell can be "abnormal" in some respect, but still be a "normal" cell for the purposes of the invention.

A "diseased" cell or tissue is one that is afflicted with a particular physiological disorder of interest.

The term "pharmaceutically acceptable" refers to any agent that is sufficiently non-toxic to cells and/or subjects to allow pharmaceutical use of the agent.

The term "pharmaceutically acceptable salt" encompasses any salt that is pharmaceutically acceptable, including alkali metal salts and addition salts of free acids or free bases.

II. Cyclooxygenase-2 Selective Agents

The invention provides cyclooxygenase-2 selective agents that can be used in the methods of the invention and/or combined with a pharmaceutically acceptable carrier to form pharmaceutical compositions.

A. Agents

A cyclooxygenase-2 selective agent according to the invention has the formula:

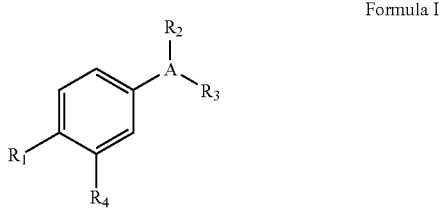

Formula I wherein:
A comprises a 4-, 5-, or 6-membered ring selected from a partially unsaturated heterocyclyl, a heteroaryl, a cycloalkenyl, and an aryl;
$R_1$ is selected from methylsulfone and sulfonamide;
$R_2$ comprises a group selected from a heteroaryl, a cycloalkyl, a cycloalkenyl, and an aryl; and
$R_3$ comprises a linear or branched alkyl; and either:
$R_3$ comprises a radioactive or paramagnetic isotope, and $R_4$ is hydrogen; or
$R_4$ comprises a radioactive or paramagnetic isotope; and
wherein the cyclooxygenase-2 selective agent is not 4-(5-[$^{18}$F]fluoromethyl-3-phenylisoxazol-4-yl)benzenesulfonamide or 4-(5-[$^{18}$F]fluoroethyl-3-phenyl-isoxazol-4-yl)benzenesulfonamide.

Isotopically labeled cyclooxygenase-2 selective agents of this type can be used for detection of cyclooxygenase-2, as described in greater detail below.

In an alternative embodiment, a cyclooxygenase-2 selective agent according to the invention has Formula I, wherein:

A comprises a 4-, 5-, or 6-membered ring selected from a partially unsaturated heterocyclyl, a heteroaryl, a cycloalkenyl, and an aryl;

$R_1$ is selected from methylsulfone and sulfonamide;

$R_2$ comprises an unsubstituted group selected from a heteroaryl, a cycloalkyl, a cycloalkenyl, and an aryl;

$R_3$ comprises a linear or branched alkyl halide; and $R_4$ is hydrogen; and wherein the cyclooxygenase-2 selective agent is not 3-[4-(methylsulfonyl)phenyl]-4-phenyl-5-trifluoromethylisoxazole, 4-(5-fluoromethyl-3-phenylisoxazol-4-yl)benzenesulfonamide, or 4-(5-fluoroethyl-3-phenylisoxazol-4-yl)benzenesulfonamide. Cyclooxygenase-2 selective agents of this type can be to inhibit cyclooxygenase-2, as described in greater detail below.

In preferred embodiments of both types (i.e., labeled and non-labeled cyclooxygenase-2 selective agents), A includes a 5-membered heterocyclic ring selected from a pyrrolyl, a furyl, an oxazolyl, an isoxazolyl, a thiazolyl, an isothiazolyl, an imidazolyl, a pyrazolyl, and the like. In particularly preferred cyclooxygenase-2 selective agents, A includes an isoxazolyl.

In certain embodiments, $R_1$ is sulfonamide. In preferred variations of these embodiments, $R_2$ is an aryl, with phenyl being particularly preferred, as in several of the cyclooxygenase-2 selective agents illustrated herein, i.e., 2-fluoro-4-(5-methyl-3-phenylisoxazol-4-yl)benzenesulfonamide, 4-[3-(4-[$^{18}$F]fluorophenyl)-5-methylisoxazol-4-yl]benzenesulfonamide (Formula IV), 4-(5-[$^{18}$F]fluoro-3-phenylisoxazol-4-yl)benzenesulfonamide (Formula V); and 4-(5-[$^{18}$F, $^{2}$H$_2$]fluoromethyl-3-phenylisoxazol-4-yl)benzenesulfonamide.

In other embodiments, $R_1$ is methylsulfone. In preferred variations of these embodiments, $R_2$ is an aryl, with phenyl being particularly preferred. Examples of cyclooxygenase-2 selective agents of this type include: 4-(4-[$^{18}$F]fluorophenyl)-3-[4-(methylsulfonyl)phenyl]-5-trifluoromethylisoxazole (Formula II) and 3-[4-(methylsulfonyl)phenyl]-4-phenyl-5-[$^{18}$F]trifluoromethylisoxazole (Formula III). The structures of exemplary forms of these compounds, labeled with $^{18}$F are shown below.

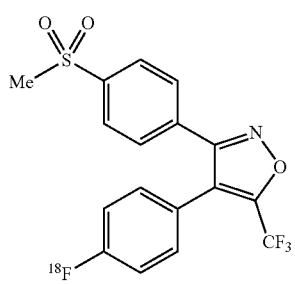

Formula II

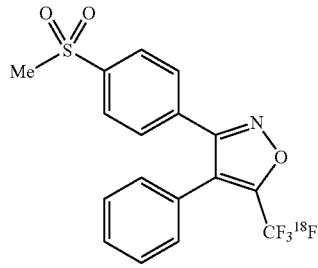

Formula III

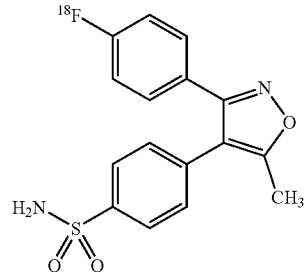

Formula IV

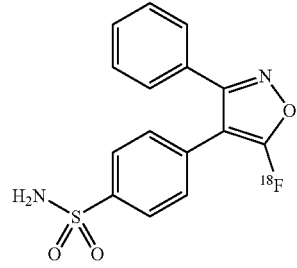

Formula V

The invention also includes salts of the above-described compounds. In the case of compounds intended for in vivo administration (e.g., for diagnostic or therapeutic uses) the salts are pharmaceutically acceptable. Suitable pharmaceutically acceptable acid addition salts of compounds of the above compounds can be prepared from an organic or inorganic acid. Examples of such inorganic acids include hydrochloric, hydrobromic, hydroiodic, nitric, carbonic, sulfuric, and phosphoric acid. Appropriate organic acids can be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, β-hydroxybutyric, salicylic, galactaric, and galacturonic acid.

Suitable pharmaceutically acceptable base addition salts of the compounds include metallic salts made from aluminum, calcium, lithium, magnesium, potassium, sodium, and zinc or organic salts made from N,N'-dibenzylethylenediamine, chloroprocaine, choline, diethanolamine, ethylenediamine, meglumine (N-methylglucamine), and procaine.

All of these addition salts can be prepared by conventional means from the corresponding compound by reacting, for example, the appropriate acid or base.

Cyclooxygenase-2 selective agents of the invention have an $IC_{50}$ for cyclooxygenase-2 that is suitable for their intended use. Cyclooxygenase-2 selective agents suitable for diagnostic or therapeutic uses generally have an $IC_{50}$ of about 50 nM or less, typically about 10 nM or less, more typically about 1 nM or less, preferably about 0.5 nM or less, more preferably about 0.1 nM or less, and most preferably 0.05 nM or less.

1. Agents for Detection of Cyclooxygenase-2

Cyclooxygenase-2 selective agents intended for use in detection of cyclooxygenase-2 are labeled with a detectable label. There are many different labels and methods of labeling known to those of ordinary skill in the art. Labels that allow quantitative detection, i.e., where the intensity of the signal from the label is proportional to the amount of cyclooxygenase-2 present are preferred. Examples of the types of labels that are particularly useful in the present invention include radioactive isotopes and paramagnetic isotopes. Cyclooxygenase-2 selective agents of the invention having Formula I, above, in which $R_3$ includes a radioactive or paramagnetic isotope, and $R_4$ is hydrogen, or in which $R_4$ includes a radioactive or paramagnetic isotope are advantageously used in cyclooxygenase-2 detection methods. Examples of cyclooxygenase-2 selective agents of this type include $^{18}F$-labelled forms of those specifically discussed above, e.g., 2-fluoro-4-(5-methyl-3-phenylisoxazol-4-yl)benzenesulfonamide. Also useful in cyclooxygenase-2 detection methods of the invention are 4-(4-[$^{18}F$]fluorophenyl)-3-[4-(methylsulfonyl)phenyl]-5-trifluoromethylisoxazole, 3-[4-(methylsulfonyl)phenyl]-4-phenyl-5-[18F]trifluoromethylisoxazole, 4-[3-(4-[$^{18}F$]fluorophenyl)-5-methylisoxazol-4-yl]benzenesulfonamide, 4-(5-[$^{18}F$]fluoro-3-phenylisoxazol-4-yl)benzenesulfonamide (Formulas II-IV, above), and 4-(5-[$^{18}F$, $^{2}H_2$]fluoromethyl-3-phenylisoxazol-4-yl)benzenesulfonamide.

For in vivo diagnostic detection, the intended imaging instrument is a major factor in selecting a given label. For example, if the device detects a radioactive isotope, the isotope must have a type of decay that is reliably detected by the imaging instrument. Another important consideration in selecting an isotope for in vivo diagnosis is that the half-life of the isotope should be long enough so that it is still detectable at the time of maximum uptake by the target, but short enough so that deleterious radiation upon the host is minimized. Ideally, an isotope used for in vivo imaging will lack a particulate emission, but will produce a large number of photons in the range of about 140 to about 515 keV, which is readily detected by conventional gamma cameras. Preferably, radiolabeled cyclooxygenase-2 selective agents of the invention have a high specific activity, e.g., more than about 1000 Ci/mmol, at the end of synthesis.

Preferred isotopes include those that are detectable by minimally invasive or non-invasive methods, such as PET and SPECT. Most preferred for non-invasive cyclooxygenase-2 imaging are cyclooxygenase-2 selective agents labeled with radioactive isotopes that are detectable by PET. Typical positron emitting nuclides like $^{11}C$, $^{73}Se$ and $^{18}F$ can be used, and short-lived positron emitters are particularly preferred, e.g., $^{11}C$ and $^{18}F$, which have half-lives of 20 and 110 minutes, respectively.

Gamma radiation-emitting isotopes like $^{76}Br$, $^{77}Br$, $^{123}I$ and $^{125}I$ can be used for the labeling of compounds to be detected by conventional scanning techniques or in SPECT. Using conventional scanning techniques, the emitted gamma radiation can be detected by a suitable device, e.g. a gamma camera, to produce images of the tissue or organ to be investigated. The more advanced SPECT technique is also based upon the detection of gamma radiation by sensible detectors.

Paramagnetic isotopes can be substituted for the above radioactive isotopes in the cyclooxygenase-2 selective agents of the invention for use in in vivo diagnostic imaging. In addition, those of ordinary skill in the art know of other labels that can be incorporated into cyclooxygenase-2 selective agents of the invention for in vivo or in vitro cyclooxygenase-2 detection, or can readily ascertain such, using routine experimentation.

All of the above-described labels can be incorporated into the cyclooxygenase-2 selective agents using standard techniques well known to those of ordinary skill in the art. For example, the $^{18}F$-labeled cyclooxygenase-2 selective agents can be synthesized by nucleophililic [$^{18}F$]fluoride substitution reaction of a proper precursor having a nitro, quternary amine, or sulfonate radical or by [18F]fluoroalkylation at a heteroatom in a cyclooxygenase-2 selective agent.

Cyclooxygenase-2 selective agents intended for use in scintigraphic imaging (e.g., PET or SPECT) preferably have plasma half-lives that are suitably short. The plasma half-life suitable for imaging depends on the physical half-life of the label. In particular, the plasma half-life is typically shorter than the physical half-life of the label. For example, $^{18}F$ has a physical half-life of about 110 minutes, and therefore unbound $^{18}F$ should be cleared from the plasma quickly, e.g., preferably on the order of less than 60 minutes.

2. Therapeutic Agents

Cyclooxygenase-2 selective agents of the invention are useful therapeutically as well as diagnostically. Preferred cyclooxygenase-2 selective agents for therapeutic use include those in which $R_2$ comprises an unsubstituted group selected from a heteroaryl, a cycloalkyl, a cycloalkenyl, and an aryl; $R_3$ comprises a linear or branched alkyl halide; and $R_4$ is hydrogen, wherein the cyclooxygenase-2 selective agent is not 3-[4-(methylsulfonyl)phenyl]-4-phenyl-5-trifluoromethylisoxazole, 4-(5-fluoromethyl-3-phenylisoxazol-4-yl)benzenesulfonamide, or 4-(5-fluoroethyl-3-phenylisoxazol-4-yl)benzenesulfonamide. Examples of cyclooxygenase-2 selective agents of this type include, e.g., 2-fluoro-4-(5-methyl-3-phenyl-isoxazol-4-yl)benzenesulfonamide. The halide is preferably selected from flourine, chlorine, bromine, and iodine, with fluorine being most preferred.

B. Synthesis

Cyclooxygenase-2 selective agents of the invention can be prepared using any of a variety of synthetic schemes, such as Synthetic Schemes I-XI described in International Publication No. WO 97/14679 (Application No. PCT/US96/16440, filed Oct. 6, 1996).

Synthetic Schemes I and II show the preparation of pyrazole-containing cyclooxygenase-2 selective agents. Similar pyrazoles can be prepared by methods described in U.S. Pat. Nos. 5,401,765; 5,434,178; 4,146,721; 5,051,518; 5,134,142; 4,914,121; and 3,984,431.

Synthetic Scheme III shows the preparation of diaryl/heteroaryl thiophenes according to methods described in U.S. Pat. Nos. 4,427,693; 4,302,461; 4,381,311; 4,590,205; and 4,820,827; and International Publication Nos. WO 95/00501 and WO94/15932. Similar pyrroles, furanones, and furans can be prepared by methods described in International Publication Nos. WO 95/00501 and WO94/15932.

Synthetic Scheme IV shows the preparation of diaryl/heteroaryl oxazoles according to methods described in U.S. Pat. Nos. 5,380,738; 3,743,656; 3,644,499; and 3,647,858; and International Publication Nos. WO 95/00501 and WO94/27980.

Synthetic Scheme V shows the preparation of diaryl/heteroaryl isoxazoles according to methods described in International Application No. PCT/US96/01869; International Publication Nos. WO92/05162 and WO92/19604; and European Patent Document No. EP 26928.

Synthetic Schemes VI and VII show the preparation of imidazole-containing cyclooxygenase-2 selective agents. Diaryl/heteroaryl imidazoles can be prepared by the methods described in U.S. Pat. Nos. 3,707,475; 3,901,908; 4,372,964; 4,472,422; 4,503,065; 4,576,958; 4,686,231; and 4,822,805; International Application No. PCT/US95/09505; International Publication Nos. WO 93/14082, WO 95/00501, and WO96/03388; and European Patent Document No. EP 372445.

Synthetic Scheme VIII shows the preparation of diaryl/heteroaryl cyclopentene cyclooxygenase-2 selective agents according to methods described in U.S. Pat. No. 5,344,991 and International Publication No. WO 95/00501.

Synthetic Scheme IX shows the preparation of 1,2-diarylbenzene cyclooxygenase-2 selective agents from 2-bromo-biphenyl intermediates (prepared, e.g., in a manner similar to that described in Synthetic Scheme VIII) and the appropriate substituted phenylboronic acids. Such terphenyl compounds can be prepared by the methods described in U.S. application Ser. No. 08/346,433.

Synthetic Scheme X shows the preparation of diaryl/heteroaryl thiazole cyclooxygenase-2 selective agents according to methods described in U.S. Pat. Nos. 4,051,250 and 4,632,930; International Publication Nos. WO96/03392 and WO 95/00501; and European Patent Document No. EP 592664. Isothiazoles can be prepared as described in International Publication No. WO 95/00501. Diaryl/heteroaryl pyridine cyclooxygenase-2 selective agents can be prepared by the methods described in U.S. Pat. Nos. 4,011,328; 4,533,666; and 5,169,857; and International Application Nos. PCT/US96/01110 and PCT/US96/01111.

The radiolabeled compounds can be prepared by methods which are known per se for related compounds by using readily available radiolabeled synthons like [$^{11}$C]—CO$_2$, [$^{11}$C]CH$_3$I, [$^{11}$C]HCN, [$^{11}$C]CO, [$^{18}$F]F$_2$, [$^{18}$F]KF, [$^{18}$F] Bu$_4$NF, [$^{18}$F]CH$_3$CO$_2$F and [$^{123}$I]NaI. Radioactive halogen can be substituted for a hydrogen and a hydroxy atom of choice in a precursor using any convenient method. International Publication No. WO 97/14679 (Application No. PCT/US96/16440, filed Oct. 6, 1996) describes several exemplary methods in Synthetic Schemes XI-XV. Synthetic Scheme XI shows the preparation of $^{18}$F-labeled cyclooxygenase-2 selective agents from nitro-substituted compounds. Synthetic Scheme XII shows the preparation of aliphatic $^{18}$F analogs by displacement of appropriately activated cycloalkyl derivatives. Synthetic Scheme XIII illustrates the incorporation of $^{11}$C from [$^{11}$C]CO$_2$ into cyclooxygenase-2 selective agents. Synthetic Scheme XIV illustrates the preparation of radioiodinated ($^{125}$I or $^{123}$I) agents by displacement of appropriate phenol derivatives. Synthetic scheme XV illustrates the preparation of radiolabeled ($^{11}$C) agents by displacement of appropriate phenol derivatives.

Also suitable for synthesizing $^{18}$F-labelled cyclooxygenase-2 selective agents is an additional scheme involving a [$^{18}$F]fluoride for trimethylammonium triflate salt exchange reaction as shown below.

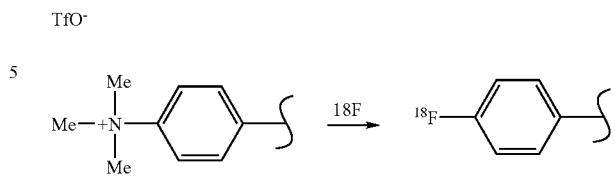

This reaction can be carried out as described in Haka, M. S.; Kilbourn, M. R.; Watkins, G. L.; Toorongian, S. A. J. Labelled Compd. Radiopharm. 1989, 27, 823-833.

III. Pharmaceutical Compositions

The cyclooxygenase-2 selective agents of the invention can be formulated in pharmaceutical compositions for diagnostic or therapeutic uses, as described in greater detail below.

A. Effective Amount

Pharmaceutical compositions of the invention include a cyclooxygenase-2 selective agent in an effective amount to achieve the intended purpose of administering the composition. For example, in an in vitro or in vivo cyclooxygenase-2 assay, an "effective amount" of a cyclooxygenase-2 selective agent refers to an amount sufficient to detect cyclooxygenase-2 under the particular assay conditions. A "diagnostically effective amount" is that amount of cyclooxygenase-2 selective agent sufficient to enable the determination of whether a physiological disorder characterized by elevated cyclooxygenase-2 expression exists. In a preferred embodiment, the amount of cyclooxygenase-2 selective agent is sufficient to enable quantitative measurement of cyclooxygenase-2 levels, which provides an indication of the severity of the disorder and/or allows monitoring of the severity of the disorder over time. Preferably, a diagnostically effective amount is one that achieves such goals while avoiding any significant adverse effects that may be observed at higher doses.

What constitutes a diagnostically effective amount varies depending on the label attached to the cyclooxygenase-2 selective agent, the method of detection (e.g., planar scintigraphy or emission tomography), and the detection site (i.e, the tissue or organ being imaged). The determination of a diagnostically effective amount for specific applications is within the level of skill in the art. In preferred embodiments, the label is a radioactive isotope. For in vivo diagnosis about 100 to about 1200 MBq, more preferably about 185 to about 1110 MBq (i.e., about 5 to about 30 mCi) of radioactively labeled cyclooxygenase-2 selective agent per 70 kg of body weight is generally sufficient, although the dose used will vary, based on the allowance for the human use dosage of the organ being imaged. Exemplary PET imaging protocols for mice and monkeys are described in the examples below.

A therapeutically effective amount of a cyclooxygenase-2 selective agent is that amount effective to prevent development of (i.e., prophylaxis) or to ameliorate, in any manner, a physiological disorder being treated (i.e., therapy). Amelioration of a physiological disorder includes amelioration of a cause or symptom of the disorder, prolongation of survival, etc. Determination of an effective amount of cyclooxygenase-2 selective agent for a given application is well within the capability of those skilled in the art, especially in light of the detailed disclosure provided herein. For example, the therapeutically effective dose of a given cyclooxygenase-2 selective agent can be estimated initially from a cell culture assays such as that described in the examples. Estimated doses can be tested in animal models where the goal is to achieve a circulating concentration range that encompasses the $IC_{50}$, as determined in cell culture, preferably with little or no toxicity. The results can be used to determine a range of effective doses in humans.

The dosage used for a particular application can vary within this range depending upon the dosage form employed and the route of administration. In addition, the exact dosage, formulation, and route of administration can be chosen by the individual physician in view of the subject's condition. (See e.g., Fingl et al., 1975, in "The Pharmacological Basis of Therapeutics," Ch. 1). Thus, the dose of cyclooxygenase-2 selective agent in the pharmaceutical compositions of the invention will, of course, depend on the goal of administration (e.g., diagnostic or therapeutic), on the characteristics of the subject being treated (e.g., the subject's weight), the type and severity of the disorder being diagnosed or treated, and the judgment of the physician. Furthermore, the dosage and interval of administration can be adjusted individually, for example, in therapeutic applications, to provide plasma levels of the cyclooxygenase-2 selective agent sufficient to maintain the desired therapeutic effects.

B. Formulation

Pharmaceutical compositions in accordance with the present invention thus can be formulated in any conventional manner using one or more physiologically acceptable carriers. The particular carrier(s) selected generally depends upon the target site for the composition and the route of administration.

For injection, the agents of the invention are conveniently formulated in an aqueous solution, preferably in a physiologically acceptable buffer, such as Hanks's solution, Ringer's solution, or a physiological saline buffer, such as phosphate-buffered saline. Oil-based injection vehicles can also be employed. Suitable vehicles of this type include, for example, fatty oils, such as sesame oil; synthetic fatty acid esters, such as ethyl oleate or triglycerides; or liposomes. Injection vehicles useful in the invention can also contain one or more suitable stabilizers or agents that increase the solubility of the cyclooxygenase-2 selective agent to allow the preparation of highly concentrated solutions. Substances that increase viscosity, such as sodium carboxymethyl cellulose, sorbitol, or dextran, can also be included in the injection vehicle. The resultant pharmaceutical compositions can include suspensions, solutions or, emulsions of one or more cyclooxygenase-2 selective agents in an aqueous or oily vehicle and can optionally contain one or more suspending and/or dispersing agents, as well as an added preservative.

Alternatively, pharmaceutical compositions according to the invention can be supplied in powder form for constitution with a suitable vehicle, e.g., sterile pyrogen-free water, before use.

Injectable pharmaceutical compositions of the invention can be administered, e.g., by bolus injection or continuous infusion. Agents intended for bolus injection can be formulated in unit dosage form, e.g., in ampules or in multidose containers.

For oral administration, the cyclooxygenase-2 selective agents can be combined with pharmaceutically acceptable carriers standardly employed for oral formulations to form tablets, pills, dragees, capsules, liquids, gels, syrups, slurries, suspensions and the like for oral ingestion by a subject. One or more solid excipients can be employed in such formulations. Examples of suitable excipients include, in particular, fillers such as sugars, including lactose, sucrose, mannitol, or sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are generally provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to tablets or dragee coatings for identification or to characterize different combinations of cyclooxygenase-2 selective agent doses.

Pharmaceutical compositions suitable for oral administration include push-fit capsules made of gelatin, as well as soft, sealed capsules made of gelatin and a plasticizer such as glycerol or sorbitol. The push-fit capsules can contain the active ingredients in admixture with a filler such as lactose, binders such as starches, and/or lubricants such as talc or magnesium stearate, and, optionally, stabilizers. In soft capsules, the active ingredients can be dissolved or suspended in one or more suitable liquids, such as fatty oils, liquid paraffin, or liquid polyethylene glycols. In addition, stabilizers can be added.

For buccal administration, tablets or lozenges formulated in conventional manner are preferred.

For transmucosal or transdermal administration, penetrants appropriate to the barrier to be permeated are preferably included in the pharmaceutical compositions. Suitable penetrants are generally known in the art.

Cyclooxygenase-2 selective agents of the invention can also be formulated in rectal compositions such as suppositories or retention enemas, e.g., containing conventional suppository bases such as cocoa butter or other glycerides.

For administration by inhalation, pharmaceutical compositions of the invention are conveniently delivered in the form of an aerosol sprayed from pressurized packs or a nebulizer, with the use of a suitable propellant, e.g., dichlorodifluoromethane, trichlorofluoromethane, dichlorotetrafluoroethane, carbon dioxide, or any other suitable gas. In the case of a pressurized aerosol, the dosage unit can be determined by providing a valve to deliver a metered amount. Capsules and cartridges, e.g., for use in an inhaler or insufflator can be formulated containing a powder mix of the cyclooxygenase-2 selective agent and a suitable powder base such as lactose or starch.

In addition, cyclooxygenase-2 selective agents can be formulated as depot preparations. Such-long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The pharmaceutical compositions of the present invention can be manufactured using standard techniques, e.g., by conventional mixing, dissolving, granulating, dragee-making, levigating, emulsifying, encapsulating, entrapping or lyophilizing processes.

IV. Cyclooxygenase-2 Detection Methods

In addition to the foregoing, the invention provides a method of detecting cyclooxygenase-2. Generally, a labeled cyclooxygenase-2 selective agent is employed to facilitate detection.

Although the method can be used to detect cyclooxygenase-2 in vitro, the method is particularly useful for in vivo detection, in which case the label is one that is detectable in vivo. In preferred embodiments, the cyclooxygenase-2 selective agent is detected by PET or SPECT, in which case, the cyclooxygenase-2 selective agent preferably includes a radioactive isotope that is readily detectable by such methods. Preferred radioactive isotopes include $^{11}C$, $^{123}I$, $^{125}I$, $^{73}Se$, $^{76}Br$, $^{77}Br$, and $^{18}F$, with $^{18}F$ being most preferred.

Preferred cyclooxygenase-2 selective agents for use in the detection method include cyclooxygenase-2 selective agents of the invention having Formula I, above, in which $R_3$ includes a radioactive or paramagnetic isotope, and $R_4$ is hydrogen, or in which $R_4$ includes a radioactive or paramagnetic isotope. Examples of cyclooxygenase-2 selective agents of this type include those specifically discussed above, e.g., the $^{18}F$-labelled form of 2-fluoro-4-(5-methyl-3-phenylisoxazol-4-yl)benzenesulfonamide. Also useful in cyclooxygenase-2 detection methods of the invention are 4-(4-[$^{18}F$]fluorophenyl)-3-[4-(methylsulfonyl)phenyl]-5-trifluoromythylisoxazole, 3-[4-(methylsulfonyl)phenyl]-4-phenyl-5-[$^{18}F$]trifluoromethylisoxazole, 4-[3-(4-[$^{18}F$]fluorophenyl)-5-methylisoxazol-4-yl]benzenesulfonamide (Formulas II-V, above), and 4-(5-[$^{18}F$, $^2H_2$]fluoromethyl-3-phenylisoxazol-4-yl)benzenesulfonamide.

For in vitro cyclooxygenase-2 assays, a cyclooxygenase-2 selective agent of the invention is added to a sample and allowed to bind to cyclooxygenase-2 present in the sample, followed by detection of the cyclooxygenase-2 selective agent as an indication of the presence or amount of cyclooxygenase-2. The cyclooxygenase-2 selective agent is added to the sample in an effective amount, i.e., one that allows detection of bound cyclooxygenase-2 selective agent under the assay conditions. The detection method of the invention also encompasses administering a diagnostically effective amount of a cyclooxygenase-2 selective agent to an individual, followed by detection of cyclooxygenase-2 in a biological sample taken from the individual or in vivo detection, preferably using a non-invasive method, such as PET or SPECT.

The cyclooxygenase-2 selective agent can be administered to the individual by any suitable route, which may depend on whether the cyclooxygenase-2 selective agent is to be detected anywhere in the individual's body or only at a specific site(s). Suitable routes of administration may, for example, include parenteral delivery, including delivery by intramuscular, subcutaneous, intramedullary, intrathecal, intraventricular, intravenous, intraperitoneal, intranasal, and intraocular injection, as well as oral, buccal, transmucosal, transdermal, or rectal administration and administration by inhalation.

The detection method can be applied to any biological sample or organism. Generally, the method will be carried out on pets or commercially valuable or research animals, especially mammals, such as primates, dogs, cats, rabbits, guinea pigs, rats, mice horses, cows, sheep, goats, pigs and the like. In addition to veterinary applications, the detection method can be employed to detect cyclooxygenase-2 in humans. Exemplary PET protocols for mice and monkeys are given in the examples below.

The detection method of the invention can be used simply to detect the presence or absence of cyclooxygenase-2, e.g., to localize a site of elevated cyclooxygenase-2 expression, or can be used to quantify the amount of cyclooxygenase-2 present in a sample or at a given site in vivo. For example, the method can be employed to identify and/or evaluate the severity of a disorder characterized by elevated cyclooxygenase-2. In addition, the method of the invention can be used to monitor the course of such a disorder in an individual. More specifically, the size or number of sites with elevated cyclooxygenase-2 levels, and/or the degree of elevation, can be measured to monitor progression of the disorder and/or determine the effectiveness of a particular therapeutic regimen aimed at amellorating the disorder.

The method encompasses the detection of cyclooxygenase-2 as an indication of inflammation and, in preferred embodiments, is carried out individuals known or suspected to have a condition selected from inflammation, arthritis, neoplasia, and a central nervous system disorder. Examples of such conditions include, but are not limited to, arthritis, e.g., rheumatoid arthritis, spondyloarthropathies, gouty arthritis, osteoarthritis, and juvenile arthritis; auto-immune disease, such as systemic iupus erytinematosus; allograft rejection; asthma; bronchitis; tendonitis; bursitis; skin-related conditions, such as psoriasis, eczema, burns and dermatitis; post-operative inflammation, including that from ophthalmic surgery such as cataract surgery and refractive surgery; gastrointestinal conditions such as inflammatory bowel disease, Crohn's disease, gastritis, irritable bowel syndrome and ulcerative colitis; neoplasia, such as colorectal cancer and cancer of the breast, lung, prostate, bladder, cervix, and skin; vascular disease; migraine headaches; periarteritis nodosa; thyroiditis; aplastic anemia; Hodgkin's disease; sclerodoma; rheumatic fever; type I diabetes; neuromuscular junction disease including myasthenia gravis; white matter disease including multiple sclerosis, sarcoidosis, nephrotic syndrome, Behcet's syndrome, polymyositis, gingivitis, and nephritis; hypersensitivity; conjunctivitis; swelling occurring after injury, myocardial ischemia; myochardial infarction; ophthalmic diseases, such as retinitis, retinopathies, uveitis, ocular photophobia, and acute injury to the eye tissue; allergic rhinitis; respiratory distress syndrome; endotoxin shock syndrome; atherosclerosis; pulmonary inflammation, such as that incident to viral and bacterial infections and cystic fibrosis; central nervous system disorders, such as cortical dementias including Alzheimer's disease, and central nervous system damage resulting from stroke, ischemia, and trauma.

V. Methods for Inhibiting Cyclooxygenase-2

The invention also includes a method of inhibiting cyclooxygenase-2 comprising binding cyclooxygenase-2 with a cyclooxygenase-2 selective agent of the invention. Cyclooxygenase-2 selective agents preferred for use in this method include those in which $R_2$ is an unsubstituted group selected from a heteroaryl, a cycloalkyl, a cycloalkenyl, and an aryl, $R_3$ is a linear or branched alkyl halide, and $R_4$ is hydrogen (excluding 3'-[4-(methylsulfonyl)phenyl]-4-phenyl-5-trifluoromethylisoxazole). Preferably, the halide is selected from fluorine, chlorine, bromine, and iodine; most preferably, the halide is fluorine.

The method entails binding an effective amount of a suitable cyclooxygenase-2 selective agent of the invention to cyclooxygenase-2, which results in enzyme inhibition, i.e., a cyclooxygenase-2 selective inhibitor. In accordance with the invention, a cyclooxygenase-2 selective inhibitor can be bound in vitro to any biological sample or fraction thereof, e.g, a blood or tissue sample, cells, or a cell lysate. The cyclooxygenase-2 selective inhibitor can, for example, be employed in research to determine biological responses that are mediated by cyclooxygenase-2.

In addition, the cyclooxygenase-2 selective inhibitor can be administered to an individual to inhibit cyclooxygenase-2 in vivo. In this embodiment, cyclooxygenase-2 is generally administered in a therapeutically effective amount for the prophylaxis or treatment of a disorder characterized by elevated cyclooxygenase-2 levels. Any of the routes of administration described above for the cyclooxygenase-2 detection method of the invention can be used, and the selection of a suitable route of administration for the prophylaxis or treatment of a particular disorder is within the level of skill of the ordinary physician.

In accordance with the invention, cyclooxygenase-2 can be inhibited in any biological sample or organism. Preferred organisms include pets or commercially valuable or research animals, as described above. In particularly preferred embodiments, the cyclooxygenase-2 inhibition method is carried out in a mammal and most preferably in a human subject.

As noted above, the cyclooxygenase-2 inhibition method of the invention can be used in the prophylaxis or treatment of a condition characterized by elevated cyclooxygenase-2 levels, such as inflammation, arthritis, neoplasia, and a central nervous system disorder. Examples of such conditions that are amenable to cyclooxygenase-2 inhibition therapy are well known and include those conditions discussed above in connection with the diagnostic method of the invention.

All publications cited herein are explicitly incorporated by reference.

EXAMPLES

The following examples are offered to illustrate, but not to limit the claimed invention.

Example 1

Cell-Based Assay For Cyclooxygenase-2 Inhibition

RAW 264.7 cells are a murine macrophage cell line that can be induced to express cyclooxygenase-2 by exposure to bacterial endotoxin/lipopolysaccharide (LPS). For this assay, RAW964.7 cells were plated at 90% confluence in 12-well cell culture plates. After attachment, cells were switched to 1 mL of endotoxin-free Dulbecco's Modified Eagle's Medium with high glucose and 0.5% calf serum overnight. Thirty minutes prior to induction of cyclooxygenase-2 expression, varying concentrations of the test compound (ranging from 20 nM to 0.3 nM) were added. NS-398 (a known cyclooxygenase-2 inhibitor) was used at 10 µM, as a control. Inhibitors or vehicle were added to the cultures by removing the existing culture medium and adding fresh medium containing inhibitor or vehicle. Cells were treated with LPS (final concentration, 10 ng per mL) to induce cyclooxygenase-2 expression. After eight hours, the media were collected from the cultures and frozen on dry ice. Cells were harvested and lysed. Protein determinations were performed to normalize $PGE_2$ values to total protein in each well. $PGE_2$ ELISA assays were performed with a commercial kit (Amersham).

Example 2

In Vivo Murine Assays for Cyclooxygenase-2 PET Probe Efficacy

A. Assay 1.

LPS-treated mice dramatically induce cyclooxygenase-2 expression in their lungs and heart. Mice (25-35 g) are intravenously injected with LPS (50 µg/mouse in saline) or with vehicle. Six hours later, all mice receive 200 µCi (7.41 MBq) of cyclooxygenase-2 PET probe in 10 µL of EtOH. Animals are then be subjected to dynamic microPET scans. See, e.g., MacLaren, D. C.; Gambhir, S. S.; Satyamurthy, N.; Barrio, J. R.; Sharfstein, S.; Toyokuni, T.; Wu, L.; Berk, A. J.; Cherry, S. R.; Phelps, M. E.; Herschman, H. R. *Gene Therapy* 1999, 8, 785-791. Animals are subsequently sacrificed. Retention of probe in the heart and lungs is determined by well counting, and induced expression of cyclooxygenase-2 is assessed by quantitative western blotting and by northern analysis.

B. Assay 2.

Xenografts of human tumors expressing constitutive cyclooxygenase-2 are injected in one subcutaneous shoulder site on the backs of nude mice, and a control tumor that does not express cyclooxygenase-2 at high levels is injected on the opposite shoulder. A549 human lung cells (a cyclooxygenase-2 producing line) and C6 glioma cells are then transplanted on the backs of mature Balb/C nude mice. When tumors have reached approximately 0.4 cm in diameter, the mice are anesthetized, injected with the cyclooxygenase-2 PET probe, and analyzed by microPET, as described above. Animals are subsequently sacrificed. Retention of probe in the two tumors is determined by well counting, and cyclooxygenase-2 expression is assessed by quantitative western blotting and by northern analysis.

Example 3

Synthesis and Testing of 2-Fluoro-4-(5-methyl-3-phenyl-isoxazol-4-yl)benzenesulfonamide A. Chemistry 2-Fluoro-4-(5-methyl-3-phenylisoxazol-4-yl)benzenesulfonamide (4) was synthesized as reported in Kumar, J. S. D.; Ho, M. M.; Leung, J. M.; Toyokuni, T. *Adv. Synth. Catal.* 2002, 344, 1146-1151. This synthesis was based on the Suzuki-cross coupling reaction. (See Ref. 1, below, for a general review of the Suzuki cross-coupling reaction.) The starting compounds 1 (Ref. 2) and 3 (Ref. 3) were prepared as reported. Melting points were measured with a Fisher-Johns melting point apparatus (Fisher Scientific, Pittsburgh, Pa.) and are uncorrected.

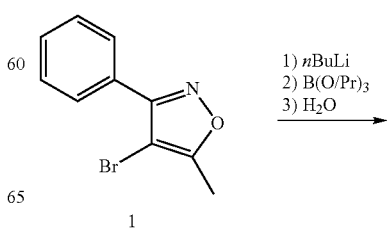

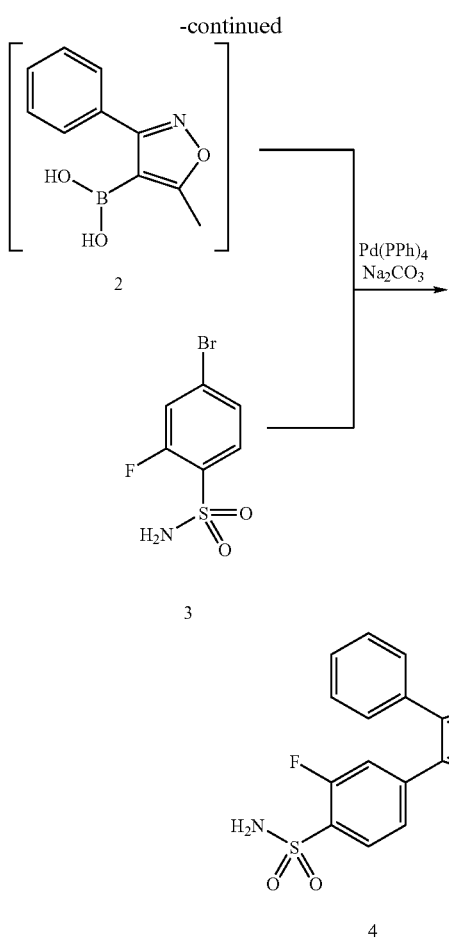

C. Synthesis of cyclooxygenase-2 PET Probe 1. 2-[$^{18}$F]Fluoro-4-(5-methyl-3-phenylisoxazol-4-yl)benzenesulfonamide Non-radioactive reference 4 is labeled with $^{18}$F by way of [$^{18}$F]fluoride ion for trimethylammonium salt exchange (see below). After protection of the sulfonamide group in 4 by a DMT group (4,4'-dimethoxytrityl), the trimethylammonium precursor is prepared by a sequence of reactions comprised of nucleophilic substitution of fluoride with dimethylamine followed by quarternisation with methyltriflate (for example, see: Damhaut, P.; Lemaire, C.; Plenevaux, A.; Brihaye, C.; Christiaens, L.; Comar, D. *Tetrahedron* 1997, 53, 5785-5796). [$^{18}$F]Fluorination with K$^{18}$F (or Bu$_4$N$^{18}$F) and the subsequent acid-catalyzed deprotection yields the desired product.

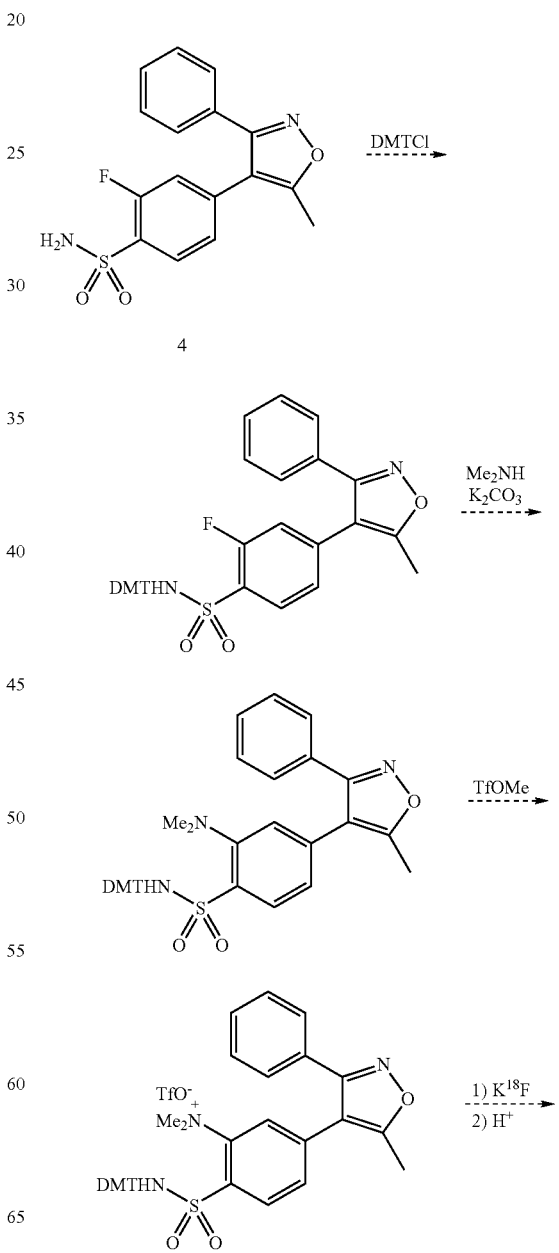

B. Synthesis of Non-Radioactive Reference

2-Fluoro-4-(5-methyl-3-phenylisoxazol-4-yl)benzenesulfonamide (4)

A 2.5 M solution of BuLi in hexane (0.48 mL, 1.2 mmol) was added to a solution of 4-bromo-5-methyl-3-phenylisoxazol (1) (240 mg, 1 mmol) in THF (5 mL) at −78° C. After 30 min, a solution of triisopropylborane (1 mL) in THF (5 mL) was added dropwise over a period of 20 min. The cooling bath was then removed and the mixture was stirred at room temperature for 2 h. The mixture was poured into brine and extracted with EtOAc. The combined EtOAc-layers were dried over anhydrous MgSO$_4$ and evaporated to give the boronic acid derivative 2 as a yellow viscous oil. To this was added 4-bromo-2-fluorobenzenesulfonamide (3) (0.15 g, 0.6 mmol), Pd(PPh$_3$)$_4$ (20 mg), EtOH (6 mL) and a 2 M solution of Na$_2$CO$_3$ in H$_2$O (1 mL) under a dry argon atmosphere. The mixture was refluxed at 80° C. for 12 h. After cooling down to room temperature, the mixture was poured into brine and extracted with EtOAc. The combined EtOAc-layers were dried over anhydrous MgSO$_4$ and evaporated to dryness. Purification by flash column chromatography over silica gel (2:3, EtOAc-hexane) gave compound 4 (140 mg, 70% from 3) as colorless powders: mp 192-195° C. (decomp). $^1$H NMR (360 MHz, CD$_3$OD) δ 2.47 (3H, s, Me), 7.09-7.12 (2H, m), 7.30-7.43 (5H, m) and 7.83 (1H, t, J=7.2 Hz) (Ar). HRMS (EI) Calculated for C$_{16}$H$_{13}$FN$_2$O$_3$S (M$^+$) 332.0630. Found: 332.0623.

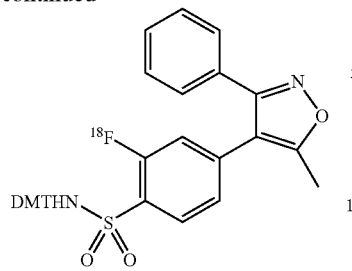

D. Biological Evaluation

The assay was carried out using lipopolysaccharide-treated murine RAW264.7 macrophages as described previously. (Refs. 4,5.) The $IC_{50}$ value for compound 4 was 1.25 to 2.5 nM.

E. References 1. (a) Miyaura, N.; Suzuki, A. "Palladium-catalyzed cross-coupling reactions of organoboron compounds." *Chem. Rev.* 1995, 95, 2457-2483. (b) Suzuki, A. "Recent advances in the cross-coupling reactions of organoboron derivatives with organic electrophiles, 1995-1998." *J. Organometal. Chem.* 1999, 576, 147-168.
2. Sokolov S D, Egorova T N. "Borodin-Hunsdiecker reaction in the isoxazole series." Khim. Geterotsikl. Soedin. 1974, 1697-1698.
3. Cheshire D, Stocks M. "Preparation of 4'-(2-hydroxy-4-pyridin-3-ylbutoxy)-biphenyl-4-sulfonamides for the treatment of asthma and rhinitis." PCT Int. Appl. WO 0018730, 2000.
4. Reddy S T, Herschman H R. "Ligand-induced prostaglandin synthesis requires expression of the TIS10/PGS-2 prostaglandin synthase gene in murine fibroblasts and macrophages." *J. Biol. Chem.* 1994, 269, 15473-15480.
5. Wadleigh D J, Reddu S T, Kopp E, Ghosh S, Herschman H R. "Transcriptional activation of the cyclooxygenase-2 gene in endotoxin-treated RAW 264.7 macrophages." *J. Biol. Chem.* 2000, 275, 6359-6266.

Example 4

Synthesis of 3-[4-(methylsulfonyl)phenyl]-4-phenyl-5-[$^{18}$F]trifluoromethylisoxazole 3-[4-(Methylsulfonyl)phenyl]-4-phenyl-5-[$^{18}$F]trifluoromethylisoxazole (9) was synthesized by nucleophilic substitution of a bromodifluoromethyl precursor with [$^{18}$F] fluoride (for example, see: Kilbourn, M. R.; Pavia, M. R.; Gregor, V. E. *Appl. Radiat. Isot.* 1990, 41, 823-828). The bromodifluoromethyl precursor 7 was prepared according to the synthetic scheme for 4-(5-methyl-3-phenylisoxazol-4-yl)benzenesulfonamide (Talley, J. J.; Brown, D. L.; Carter, J. S.; Graneto, M. J.; Koboldt, C. M.; Masferrer, J. L.; Perkins, W. E.; Rogers, R. S.; Shaffer, A. F.; Zhang, Y. Y.; Zweifel, B. S.; Seivert, K. *J. Med. Chem.* 2000, 43, 775-777) starting from the known oxime 5 (Matsumoto, A.; Oka, H.; Ohwa, M.; Kura, H.; Birbaum, J.-L.; Dietliker, K. Ger. Offen. DE 19928742), except for the use of ethyl bromodifluoroacetate in the place of ethyl acetate, followed by oxidation with Oxone® (Habeeb, A. G.; Rao, P. N. P.; Knaus, E. E. *Drug Dev. Res.* 2000, 51, 273-286).

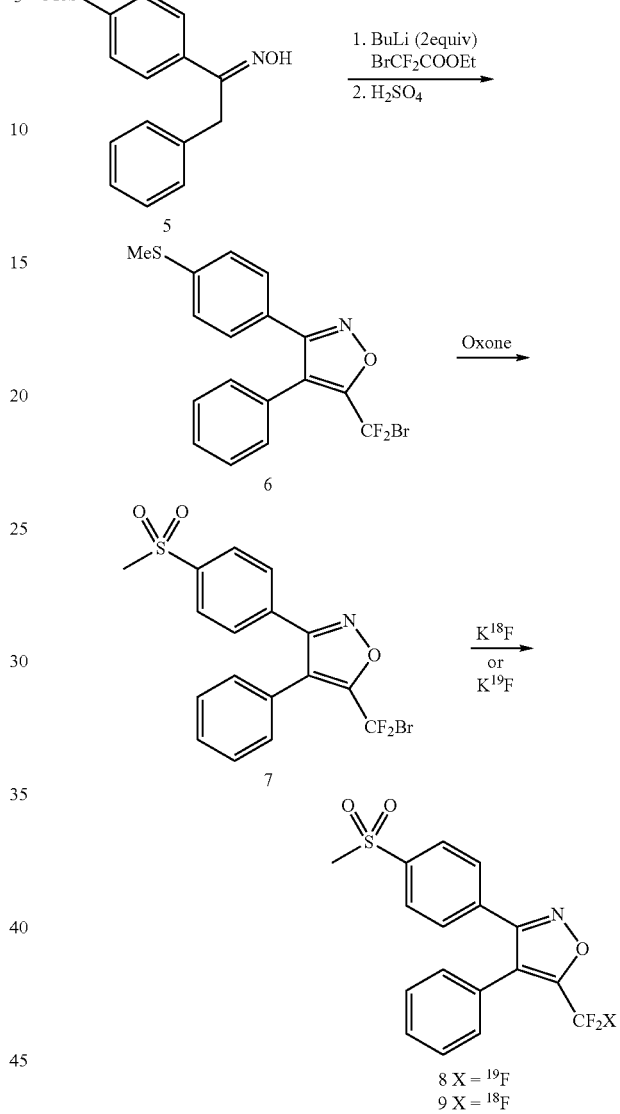

A. General $^1$H NMR spectra were recorded on a Bruker AM-360 WB spectrometer. Chemical shift standards were internal TMS. High resolution mass spectrometry (HRMS) was measured on a ZAB SE mass spectrometer using a FAB mode. Flash column chromatography was performed with ICN silica gel 60 (0.032-0.063 mm). HPLC was performed using a Knauer HPLC pump K-501 and a Knauer UV detector K-2501 (254 nm). Radioactivity was monitored with a Bioscan Flow-Count™ system FC-7700 containing a FC-3300 detector.

B. Synthesis of Non-Radioactive Reference 8

1. 5-(Bromodifluoromethyl)-3-(4-methylsulfanylphenyl)-4-phenylisoxazole (6)

Lithium diisopropylamide, prepared from n-BuLi (2.5 mmol) and diisopropylamine (2.5 mmol), was added dropwise to a solution of 1-(4-methylsulfanylphenyl)-2-phenylethanone oxime (5) (257 mg, 1 mmol) in dry THF (25 mL)

at −20° C. The reaction mixture was stirred at −20° C. for 1 h and then allowed to warm to room temperature for 1 h. The reaction mixture was cooled to −78° C. and ethyl bromodifluoroacetate (153 µL, 1.2 mmol) was added in one portion. After 5 h at −78° C., the reaction mixture was allowed to warm to room temperature, diluted with 1M HCl (10 mL) and extracted with $CH_2Cl_2$. The organic extracts were dried over anhydrous $MgSO_4$, filtered and concentrated to dryness. The yellow residue was then treated with concentrated $H_2SO_4$ (25 mL) at 0° C. overnight. The reaction mixture was poured over ice-cold $H_2O$ and extracted with $CH_2Cl_2$. The organic extracts were dried over anhydrous $MgSO_4$, filtered and concentrated. Purification by flash column chromatography with hexanes-EtOAc (4:1) yielded 6 (47 mg, 12%) as a colorless syrup: $^1$H NMR ($CDCl_3$) δ 2.52 (3H, s, SMe), 7.23-7.50 (9H, m, Ar). HRMS (FAB) Calculated for $C_{17}H_{13}BrF_2NOS$ ($MH^+$, 395.9865). Found: 395.9861.

2. 5-(Bromodifluoromethyl)-3-(4-methanesulfonylphenyl)-4-phenylisoxazole (7)

A mixture of Oxone® (120 mg), $H_2O$ (3 mL) and MeOH (1 mL) was added dropwise to a solution of 6 (43 mg, 0.108 mmol) in THF (5 mL) with stirring. The reaction mixture was stirred for 2 h and diluted with $H_2O$ (10 mL). The product was extracted with $CH_2Cl_2$ and the organic extracts were dried over anhydrous $MgSO_4$. After filtration, the filtrate was concentrated and the resulting residue was purified by flash column chromatography with hexanes-EtOAc (4:1) to give 7 (39 mg, 81%) as a colorless solid: $^1$H NMR ($CDCl_3$) δ 3.11 (3H, s, $SO_2Me$), 7.27-7.98 (9H, m, Ar). HRMS (FAB) Calculated for $C_{17}H_{13}BrF_2NO_3S$ ($MH^+$, 427.9766). Found: 427.9765.

3. 3-(4-Methanesulfonylphenyl)-4-phenyl-5-trifluoromethylisoxazole (8)

A mixture of 7 (5.4 mg, 0.013 mmol), anhydrous KF (1.1 mg, 0.019 mmol), Kryptofix® 222 (7.0 mg, 0.019 mmol) and dry MeCN (1.0 mL) was refluxed for 50 min. The reaction mixture was diluted with $H_2O$ (5 mL) and passed through a Waters Sep-Pak® C-18 cartridge (1 mL). The cartridge was washed with $H_2O$ (3×3 mL) and with MeCN (3 mL). The MeCN eluate was purified by semi-preparative HPLC (Phenomenex® HPLC column: aqua, 5µ, C-18, 10 mm×250 mm) with MeCN—$H_2O$ (3:1) containing 0.075% TFA (5 mL/min). The fractions at 22-25 min were combined and concentrated to yield 8 (2.3 mg, 50%) as a colorless solid. The $^1$H NMR spectrum was identical with those reported (Habeeb, A. G.; Rao, P. N. P.; Knaus, E. E. *Drug Dev. Res.* 2000, 51, 273-286).

C. Synthesis of cyclooxygenase-2 PET Probe 9

1. 3-(4-Methanesulfonylphenyl)-4-phenyl-5-[$^{18}$F]trifluoromethylisoxazole (9)

No carrier added [$^{18}$F]fluoride (>500 mCi or >18.5 GBq; specific radioactivity: >10,000 Ci/mmol or >0.37 PBq/mmol) was produced by 11 MeV proton bombardment of 95% $^{18}$O-enriched $H_2O$ via $^{18}O(p,n)^{18}F$ nuclear reaction using a CS-22 Cyclotron. The radioactivity (~500 mCi or ~18.5 GBq) was transferred to a reaction vessel containing Kryptofix® 222 (7 mg) and $K_2CO_3$ (0.7 mg) in MeCN—$H_2O$ (25:1, 0.7 mL). After $H_2O$ was evaporated at 105° C. with a stream of $N_2$ (nitrogen) gas, the residue was dried further by azeotropic distillation with MeCN (4×0.2 mL). The 12.5-mM stock solution of compound 16 in MeCN (1.0 mL) was added, and the mixture was heated to 90° C. for 45 min. After the addition of $H_2O$ (4 mL), the mixture was placed on a Waters Sep-Pak® C-18 cartridge (1 mL), washed with $H_2O$ (3×4 mL), and eluted with MeCN (3 mL). The MeCN eluate was purified by semi-preparative HPLC (Phenomenex® HPLC column: aqua, 5µ, C-18, 10 mm×250 mm) with MeCN—$H_2O$ (3:1) containing 0.075% TFA (5 mL/min). The chemically and radiochemically pure fraction (~15 mL; retention time: 23-26 min.) was collected to give compound 9 (~12 mCi or ~0.44 GBq). The total synthesis time was ~100 min from the end of bombardment and the decay-corrected yield was ~5%. The chemical and radiochemical purity as well as chemical identity of compound 9 was confirmed using analytical HPLC (Phenomenex® HPLC column: aqua, 5 µl, C-18, 4.6 mm×250 mm) with MeCN—$H_2O$ (3:1) containing 0.075% TFA (1 mL/min) by reference to the non-radioactive compound 8 (retention time: 12 min).

Example 5

Synthesis of 4-(4-[$^{18}$F]fluorophenyl)-3-[4-(methylsulfonyl)phenyl]-5-trifluoromethylisoxazole 4-(4-[$^{18}$F]fluorophenyl)-3-[4-(methylsulfonyl)phenyl]-5-trifluoromethylisoxazole is synthesized via [$^{18}$F]fluoride displacement of the nitro group in a 4-nitrophenyl precursor (for example, see: Kilbourn, M. R.; Dence, C. S.; Welch, M. J.; Mathias, C. J. *J. Nucl. Med.* 1987, 28, 462-470). Synthesis of the precursor follows the synthetic scheme for 3-[4-(methylsulfonyl)phenyl]-4-phenyl-5-trifluoromethylisoxazole (Habeeb, A. G.; Rao, P. N. P; Knaus, E. E. *Drug Dev. Res.* 2000, 51, 273-286), where 3-phenyl-1,1,1-trifluoropropan-2-one is replaced with 3-(4-nitrophenyl)-1,1,1-trifluoropropan-2-one, prepared by Grignard reaction of ethyl trifluoroacetate with 4-nitrobenzylmagnesium bromide (Song, Z. Z.; Wong, H. N. C.; *Liebigs Ann. Chem.* 1994, 29-34).

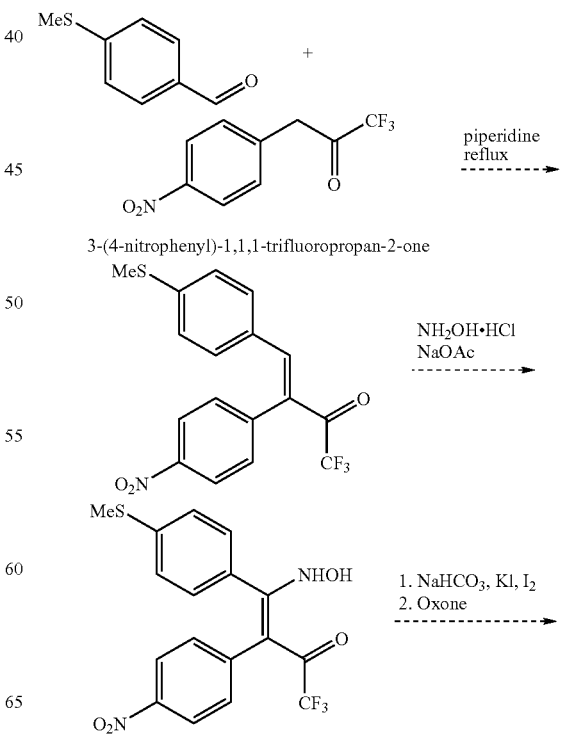

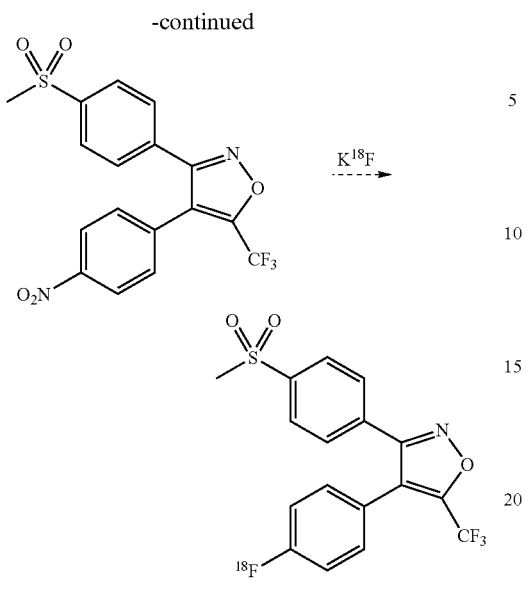

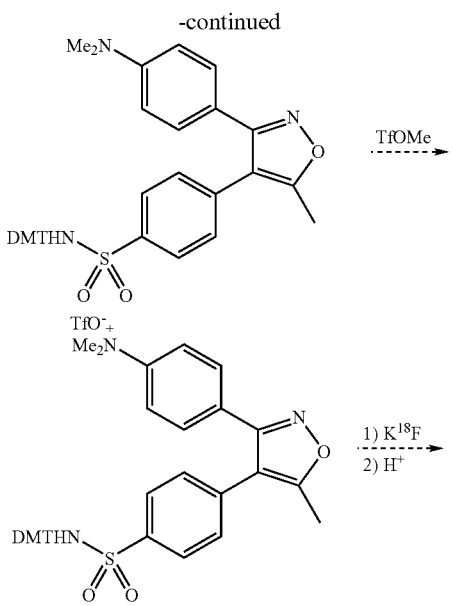

Example 6

Synthesis of 4-[3-(4-[$^{18}$F]fluorophenyl)-5-methyl-isoxazol-4-yl]benzenesulfonamide 4-[3-(4-[$^{18}$F]fluorophenyl)-5-methylisoxazol-4-yl]benzenesulfonamide is synthesized using a [$^{18}$F]fluoride ion for trimethylammonium salt exchange reaction. A trimethylammonium triflate precursor will be prepared from the non-radioactive 4-[3-(4-fluorophenyl)-5-methylisoxazol-4-yl]benzenesulfonamide (Talley, J. J. U.S. Pat. No. 5,859,257) by a sequence of reactions consisting of nucleophilic substitution of fluoride with dimethylamine followed by quarternisation with methyltriflate (Damhaut, P.; Lemaire, C.; Plenevaux, A.; Brihaye, C.; Christiaens, L.; Comar, D. *Tetrahedron* 1997, 53, 5785-5796).

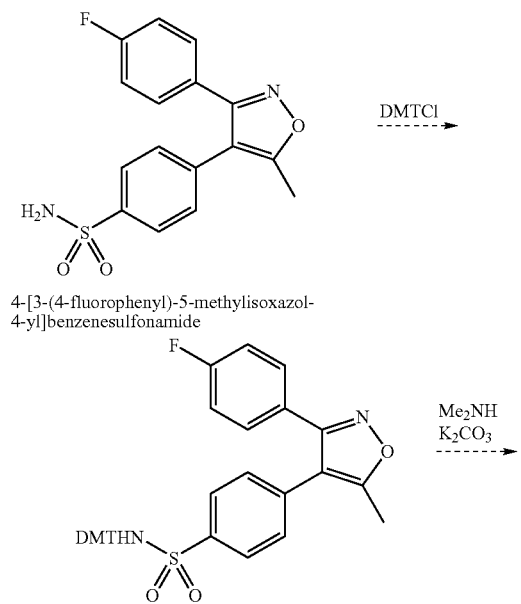

Example 7

Synthesis of 4-(5-[$^{18}$F]fluoro-3-phenylisoxazol-4-yl)benzenesulfonamide 4-(5-[1$^8$F]fluoro-3-phenylisoxazol-4-yl)benzenesulfonamide is synthesized by [$^{18}$F]fluoride displacement of a triflate group (for example, see: Hamacher, K.; Coenen, H. H.; Stöcklin, G. *J. Nucl. Med.* 1985, 27, 235-238). The triflate precursor will be prepared by triflation of 4-(5-hydroxy-3-phenylisoxazol-4-yl)benzenesulfonamide (Talley, J. J. U.S. Pat. No. 5,859,257) with triflic anhydride.

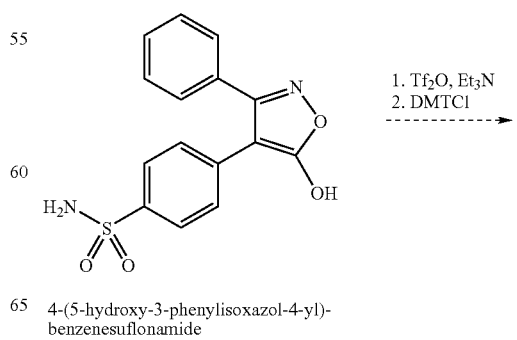

4-(5-hydroxy-3-phenylisoxazol-4-yl)-benzenesuflonamide

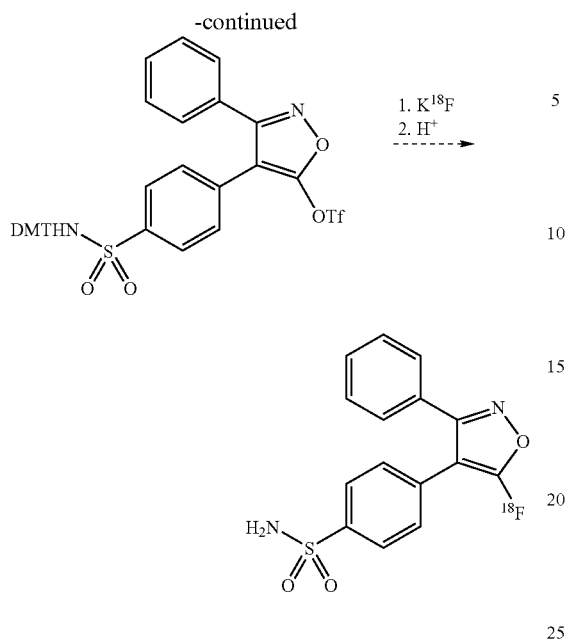

Example 8

Synthesis of 4-(5-[$^{18}$F, $^2$H$_2$]-fluoromethyl-3-phenyl-isoxazol-4-yl)benzenesulfonamide To synthesize 4-(5-[$^{18}$F, $^2$H$_2$]fluoromethyl-3-phenylisoxazol-4-4-yl)benzenesulfonamide, the key intermediate, 4-(5-[$^2$H$_2$]chloromethyl-3-phenylisoxazol-4-yl)benzenesulfonamide (10), is synthesized according to the synthetic scheme reported for its non-deuterated counterpart 4-(5-chloromethyl-3-phenylisoxazol-4-yl)benzenesulfonamide (Talley, J. J.; Brown, D. L.; Carter, J. S.; Graneto, M. J.; Koboldt, C. M.; Masferrer, J. L.; Perkins, W. E.; Rogers, R. S.; Shaffer, A. F.; Zhang, Y. Y.; Zweifel, B. S.; Seivert, K. *J. Med. Chem.* 2000, 43, 775-777) using methyl [$^2$H$_2$]chloroacetate (11) in the place of methyl chloroacetate. The deuterated methyl chloroacetate 11 is prepared from commercially available acetic acid-d$_4$ as reported (Baldwin, J. E.; Cianciosi, S. J. *J. Am. Chem. Soc.* 1992, 114, 9401-9408). After protection of the sulfonamide group with 4,4'-dimethoxyltrityl (DMT) group, treatment with silver tosylate yields the [$^{18}$F]fluorination precursor 12 (for example, see: Tewson, T. J.; Stekhova, S.; Kinsey, B.; Chen, L.; Wiens, L.; Barber, R. *Nucl. Med. Biol.* 1999, 26, 891-896). [$^{18}$F]Fluorination by [$^{18}$F]fluoride-for-tosyloxy substitution reaction, followed by acidic treatment to remove the DMT group, yields the cyclooxygenase-2 PET probe 13, i.e., 4-(5-[$^{18}$F, $^2$H$_2$]fluoromethyl-3-phenylisoxazol-4-yl)benzenesulfonamide.

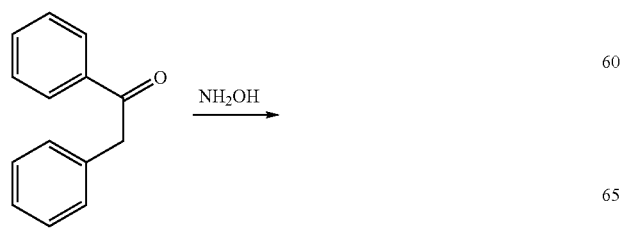

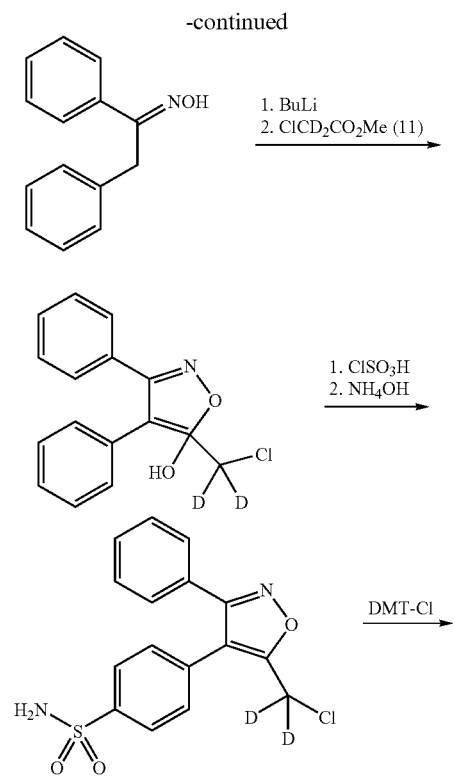

Key Intermediate 10

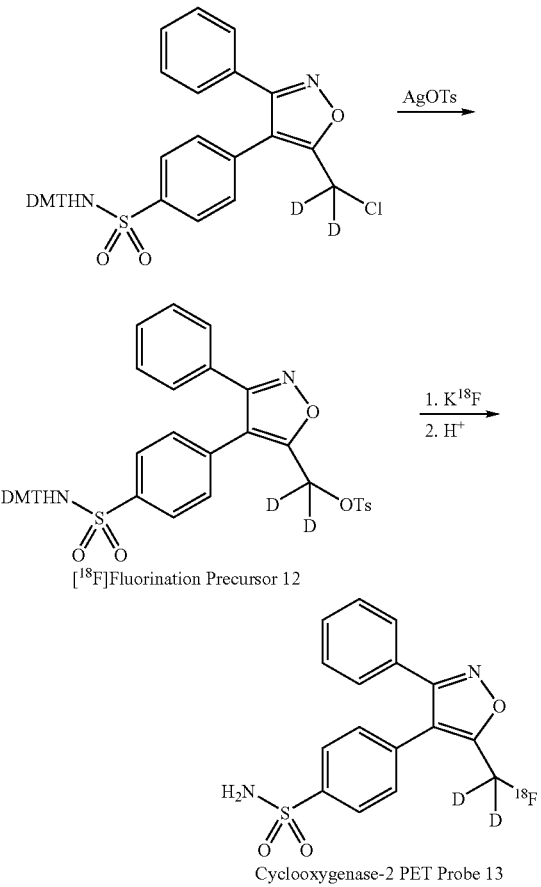

[$^{18}$F]Fluorination Precursor 12

Cyclooxygenase-2 PET Probe 13

Example 9

PET Protocol for Monkeys

On the evening prior to the PET study, monkeys are fasted after 9 PM. The morning of the study, all equipment is sterilized, the animal examined, and its condition noted. If the animal is found to be in a normal state, initial anesthetization is carried out with 15-20 mg/Kg ketamine i.m.. Animals are then transported to the PET Laboratory. A peripheral intravenous line is placed in the tail, and the animal is either infused with 15-20 mg/Kg/hr of ketamine with bolus delivery of 0.2-0.3 mg/Kg/hr midazolam or maintained anesthetically by inhalant isofluorane techniques (1-2%).

Animals are studied using a PET Scanner developed by Concorde System that collects 3-D data with an axial span of ~8 centimeters. Animals are placed supine in the tomograph bed with head in the gantry on a custom cradle designed to support the head and prevent head movement. Approximately 1.5 mCi/Kg of imaging agent is administered intravenously. A dynamic scanning protocol for a specific tissue or region (10×90 sec and 21×300 sec) over 120 min is performed for $^{18}$F labeled compounds. For whole body distribution measurements, a series of bed positions will be used to cover the entire animal, with each position (300 s frames) repeated 3-6 times per experiments. Images will be reconstructed with a reconstruction filter that gives an in-plane resolution of 2.0 mm. At the completion of the emission scan, the intravascular catheters are removed and the arterial puncture site held until bleeding is stopped and then taped with a pressure bandage. Emission scans are corrected for attenuation using calculated attenuation method based on the tissue cross-section determined from the image sinograms or measured using a rotating rod source. During the study, pulse rate and blood oxygenation is monitored with an oxymeter. Body temperature is monitored constantly with a heating blanket.

Example 10

PET Protocol for Mice

Mice are imaged using a similar protocol described above. Blood sampling is infrequent and by tail vein or cardiac stick to verify image-based input function estimates. Anesthesia is 10-mg/kg xylazine with 200-mg/kg ketamine. The imaging system has sufficient axial length to image the mouse in one bed position, providing whole body distribution and organ uptake estimates in a single dynamic experiment. Frame times and sequence will be as above (10×90 sec and 21×300 sec for 18F).

What is claimed is:

1. A cyclooxygenase-2 selective agent having the formula:

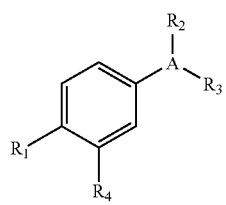

wherein:
A is a 4-, 5-, or 6-membered ring selected from the group consisting of partially unsaturated heterocyclyl, heteroaryl, cycloalkenyl, and aryl;
$R_1$ is selected from methylsulfone and sulfonamide;
$R_2$ is-selected from heteroaryl, cycloalkyl, cycloalkenyl, and aryl; and
$R_3$ is a linear or branched alkyl; and either:
$R_3$ contains a radioactive or paramagnetic isotope, and $R_4$ is hydrogen; or
$R_4$ is or contains a radioactive or paramagnetic isotope; and
wherein the cyclooxygenase-2 selective agent is not 4-(5-[$^{18}$F]fluoromethyl-3-phenylisoxazol-4-yl)benzenesulfonamide or 4-(5-[$^{18}$F]fluoroethyl-3-phenylisoxazol-4-yl)benzenesulfonamide.

2. The cyclooxygenase-2 selective agent of claim 1 wherein $R_3$ contains a radioactive or paramagnetic isotope, and $R_4$ is hydrogen.

3. The cyclooxygenase-2 selective agent of claim 1 wherein $R_4$ is a radioactive or paramagnetic isotope.

4. The cyclooxygenase-2 selective agent of claim 1 wherein A is a 5-membered heterocyclic ring selected from a pyrrolyl, a furyl, an oxazolyl, an isoxazolyl, a thiazolyl, an isothiazolyl, an imidazolyl, and a pyrazolyl.

5. The cyclooxygenase-2 selective agent of claim 4 wherein A is an isoxazolyl ring.

6. The cyclooxygenase-2 selective agent of claim 1 wherein $R_1$ is sulfonamide.

7. The cyclooxygenase-2 selective agent of claim 1 wherein $R_1$ is methylsulfone.

8. The cyclooxygenase-2 selective agent of claim 1 wherein $R_2$ is an unsubstituted aryl.

9. The cyclooxygenase-2 selective agent of claim 8 wherein $R_2$ is phenyl.

10. The cyclooxygenase-2 selective agent of claim 1 wherein either:
$R_3$ contains a radioactive halide, and $R_4$ is hydrogen; or
$R_4$ is or contains a radioactive halide.

11. The cyclooxygenase-2 selective agent of claim 1 wherein the cyclooxygenase-2 selective agent contains a radioactive isotope and has a specific activity of at least about $10^3$ Ci/mmol.

12. The cyclooxygenase-2 selective agent of claim 11 wherein the isotope is detectable by PET.

13. The cyclooxygenase-2 selective agent claim 11 wherein the isotope is selected from $^{11}$C, $^{123}$I, $^{125}$I, $^{73}$Se, $^{76}$Br, $^{77}$Br, and $^{18}$F.

14. The cyclooxygenase-2 selective agent of claim 13 wherein the isotope is $^{18}$F.

15. The cyclooxygenase-2 selective agent of claim 1 wherein the cyclooxygenase-2 selective agent is a cyclooxygenase-2 inhibitor with an $IC_{50}$ of less than about 10 nM.

16. The cyclooxygenase-2 selective agent of claim 1 wherein the cyclooxygenase-2 selective agent is selected from 2-[$^{18}$F]fluoro-4-(5-methyl-3-phenylisoxazol-4-yl)benzenesulfonamide and 3-[4-(methylsulfonyl)phenyl]-4-phenyl-5-[$^{18}$F]trifluoromethylisoxazole.

17. A pharmaceutical composition comprising a pharmaceutically acceptable carrier and a diagnostically effective amount of a cyclooxygenase-2 selective agent having the formula:

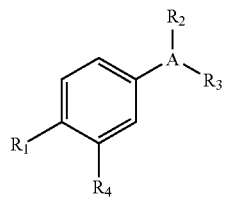

wherein:
A is a 4-, 5-, or 6-membered ring selected from the group consisting of partially unsaturated heterocyclyl, heteroaryl, cycloalkenyl, and aryl;
$R_1$ is selected from methylsulfone and sulfonamide;
$R_2$ is selected from heteroaryl, cycloalkyl, cycloalkenyl, and aryl; and
$R_3$ contains a linear or branched alkyl; and either:
$R_3$ is a radioactive or paramagnetic isotope, and $R_4$ is hydrogen; or
$R_4$ is or contains a radioactive or paramagnetic isotope; and
wherein the cyclooxygenase-2 selective agent is not 4-(5-[$^{18}$F]fluoromethyl-3-phenylisoxazol-4-yl)benzenesulfonamide or 4-(5-[$^{18}$F]fluoroethyl-3-phenylisoxazol-4-yl)benzenesulfonamide.

18. The pharmaceutical composition of claim 17 wherein $R_3$ contains a radioactive or paramagnetic isotope, and $R_4$ is hydrogen.

19. The pharmaceutical composition of claim 17 wherein $R_4$ is a radioactive or paramagnetic isotope.

20. The pharmaceutical composition of claim 17 wherein A is a 5-membered heterocyclic ring selected from a pyrrolyl, a furyl, an oxazolyl, an isoxazolyl, a thiazolyl, an isothiazolyl, an imidazolyl, and a pyrazolyl.

21. The pharmaceutical composition of claim 20 wherein A is an isoxazolyl ring.

22. The pharmaceutical composition of claim 17 wherein $R_1$ is sulfonamide.

23. The pharmaceutical composition of claim 17 wherein $R_1$ is methylsulfone.

24. The pharmaceutical composition of claim 17 wherein $R_2$ is an unsubstituted aryl.

25. The pharmaceutical composition of claim 24 wherein $R_2$ is phenyl.

26. The pharmaceutical composition of claim 17 wherein either:
$R_3$ contains a radioactive halide, and $R_4$ is hydrogen; or
$R_4$ is or contains a radioactive halide.

27. The pharmaceutical composition of claim 17 wherein the cyclooxygenase-2 selective agent contains a radioactive isotope and has a specific activity of at least about 103 Ci/mmol.

28. The pharmaceutical composition of claim 27 wherein the isotope is detectable by PET.

29. The pharmaceutical composition of claim 27 wherein the isotope is selected from $^{11}$C, $^{123}$I, $^{125}$I, $^{73}$Se, $^{76}$Br, $^{77}$Br, and $^{18}$F.

30. The pharmaceutical composition of claim 29 wherein the isotope is $^{18}$F.

31. The pharmaceutical composition of claim 17 wherein the cyclooxygenase-2 selective agent is a cyclooxygenase-2 inhibitor with an $IC_{50}$ of less than about 10 nM.

32. The pharmaceutical composition of claim 17 wherein the cyclooxygenase-2 selective agent is selected from 2-fluoro-4-(5-methyl-3-phenylisoxazol-4-yl)benzenesulfonamide and 3-[4-(methylsulfonyl)phenyl]-4-phenyl-5-[$^{18}$F]trifluoromethylisoxazole.

33. The cyclooxygenase-2 selective agent of any one of claims 1, 2, 4-6, and 8-11 wherein $R_3$ contains deuterium.

34. The cyclooxygenase-2 selective agent of claim 1 wherein the cyclooxygenase-2 selective agent is 4-(5-[$^{18}$F, $^2$H$_2$]fluoromethyl-3-phenylisoxazol-4-yl)benzenesulfonamide.

35. The pharmaceutical composition of any of claims 17, 18, 20-22, and 24-27 wherein $R_3$ contains deuterium.

36. The pharmaceutical composition of claim 17 wherein the cyclooxygenase-2 selective agent is 4-(5-[$^{18}$F, $^2$H$_2$]fluoromethyl-3-phenylisoxazol-4-yl)benzenesulfonamide.

37. A cyclooxygenase-2 selective agent having the formula:

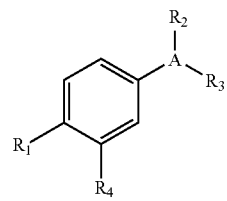

wherein:
A is a 4-, 5-, or 6-membered ring selected from the group consisting of partially unsaturated heterocyclyl, heteroaryl, cycloalkenyl, and aryl;
$R_1$ is selected from methylsulfone and sulfonamide;
$R_2$ is selected from heteroaryl, cycloalkyl, cycloalkenyl, and aryl;
$R_3$ is a linear or branched alkyl; and
$R_4$ is or contains a radioactive or paramagnetic isotope; and
wherein the cyclooxygenase-2 selective agent is not 4-(5-[$^{18}$F]fluoromethyl-3-phenylisoxazol-4-yl)benzenesulfonamide or 4-(5-[$^{18}$F]fluoroethyl-3-phenylisoxazol-4-yl)benzenesulfonamide.

38. The cyclooxygenase-2 selective agent of claim 37, wherein $R_3$ contains a radioactive halogen.

39. The cyclooxygenase-2 selective agent of claim 1, wherein $R_3$ is methyl.

* * * * *

UNITED STATES PATENT AND TRADEMARK OFFICE
CERTIFICATE OF CORRECTION

PATENT NO. : 7,329,401 B2
APPLICATION NO. : 10/341316
DATED : February 12, 2008
INVENTOR(S) : Tatsushi Toyokuni et al.

It is certified that error appears in the above-identified patent and that said Letters Patent is hereby corrected as shown below:

On the Title Page

| | |
|---|---|
| Item -56- References Cited, OTHER PUBLICATIONS, pg. 2, | After "©", Insert --2000-- |
| Column 33, line 53, Claim 27 | Delete "103", Insert --$10^3$-- |

Signed and Sealed this

Twenty-second Day of July, 2008

JON W. DUDAS
*Director of the United States Patent and Trademark Office*